(12) United States Patent
Takahashi

(10) Patent No.: US 9,562,234 B2
(45) Date of Patent: Feb. 7, 2017

(54) METHOD FOR THE PRODUCTION OF DUPLICATION AND TRANSLOCATION OF ANY REGION IN THE CHROMOSOME OF ASPERGILLUS

(71) Applicant: Kikkoman Corporation, Chiba (JP)

(72) Inventor: Tadashi Takahashi, Chiba (JP)

(73) Assignee: KIKKOMAN CORPORATION, Chiba (JP)

( * ) Notice: Subject to any disclaimer, the term of this patent is extended or adjusted under 35 U.S.C. 154(b) by 0 days.

(21) Appl. No.: 13/856,763

(22) Filed: Apr. 4, 2013

(65) Prior Publication Data
US 2013/0316065 A1    Nov. 28, 2013

(30) Foreign Application Priority Data

Apr. 7, 2012 (JP) .................................. 2012-87987
Mar. 15, 2013 (JP) ................................. 2013-052795

(51) Int. Cl.
*C12N 15/80* (2006.01)

(52) U.S. Cl.
CPC ............... *C12N 15/80* (2013.01); *A23L 27/50* (2016.08)

(58) Field of Classification Search
None
See application file for complete search history.

(56) References Cited

U.S. PATENT DOCUMENTS 6,352,841 B1 * 3/2002 Lehmbeck .................. 435/69.1
2006/0253918 A1   11/2006 Que

FOREIGN PATENT DOCUMENTS

| EP | 2 584 031 | 4/2013 |
| JP | 2009-95279 | 5/2009 |
| JP | 4469014 | 3/2010 |
| WO | WO 9845455 A1 * | 10/1998 |
| WO | 2011/158623 | 12/2011 |

OTHER PUBLICATIONS

J. Argueso et al., "Double-strand breaks associated with repetitive DNA can reshape the genome", PNAS, vol. 105, No. 33, pp. 11845-11850, Aug. 19, 2008.
European Search Report issued Sep. 20, 2013 in European Application No. 13 16 2003.
You et al., "Gene-specific disruption in the filamentous fungus *Cercospora nicotianae* using a split-marker approach", Archives of Microbiology, vol. 191, 2009, pp. 615-622.
Agmon et al., "Analysis of repair mechanism choice during homologous recombination", Nucleic Acids Research, vol. 37, No. 15, 2009, pp. 5081-5092.

* cited by examiner

*Primary Examiner* — Mindy G Brown
(74) *Attorney, Agent, or Firm* — Wenderoth, Lind & Ponack, L.L.P.

(57) ABSTRACT

The purpose of the present invention is to provide a technique to duplicate and translocate any large region in a chromosome of a fungus belonging to *Aspergillus* across a wide range, so that it will possible to stably and systematically acquire an *Aspergillus* strain having a novel trait, which was un-acquirable by conventional techniques.
The present invention relates to a transformant of the fungus belonging to *Aspergillus* wherein a transformation marker gene with deficiency of a terminal part at the 5' or 3' end of its coding region is integrated into an outside of a target region in a chromosome of the fungus subject to duplicated translocation, and a transformation marker gene with deficiency of a terminal part at the 3' or 5' end of its coding region is integrated into an outside of a region in another chromosome of the fungus to be replaced with the target region.

15 Claims, 11 Drawing Sheets

Fig.3 Target region before the duplicated translocation in chromosome

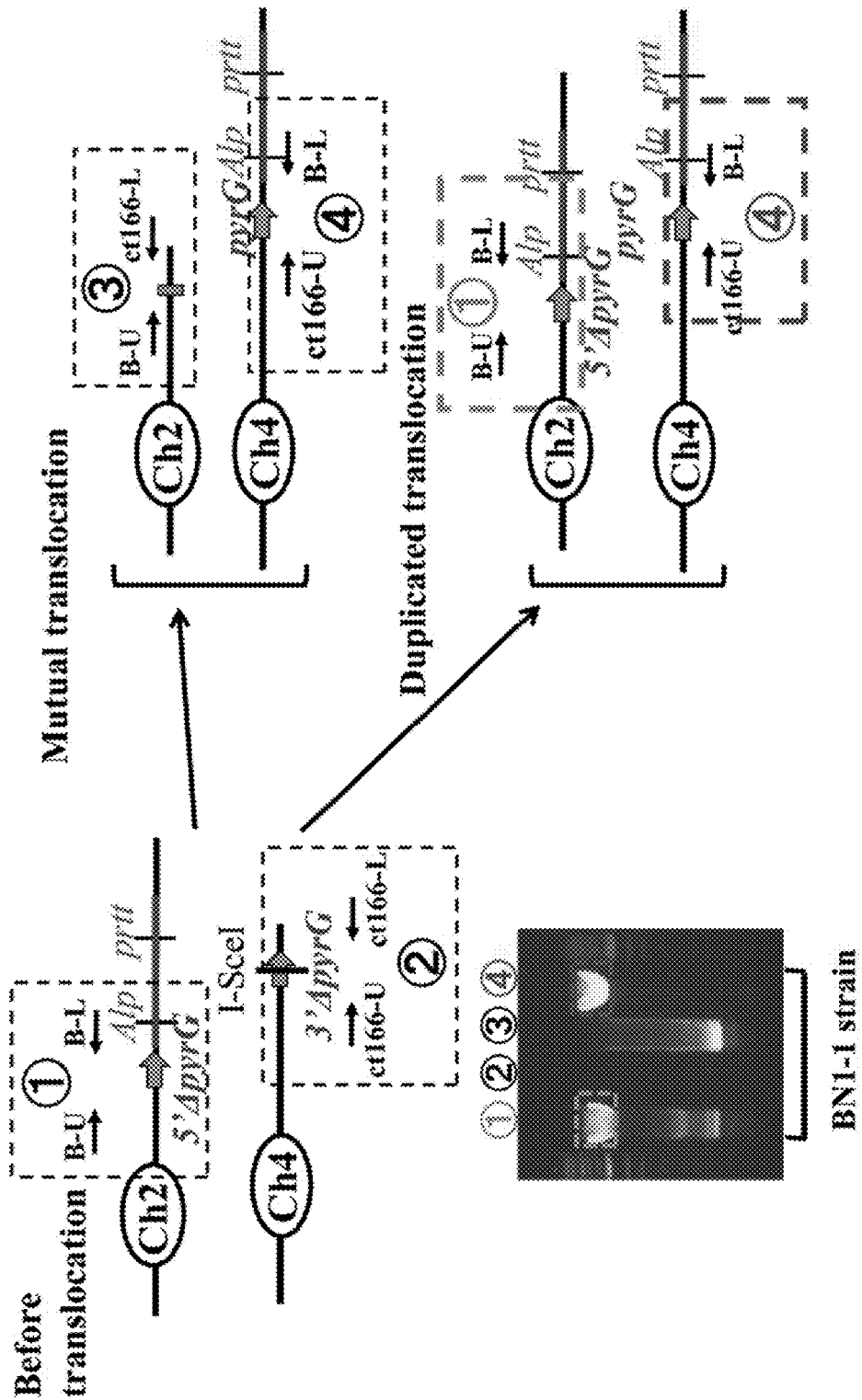
Fig.9 Acquisition of a strain having the translocation of the duplicated region by site-specific cleavage

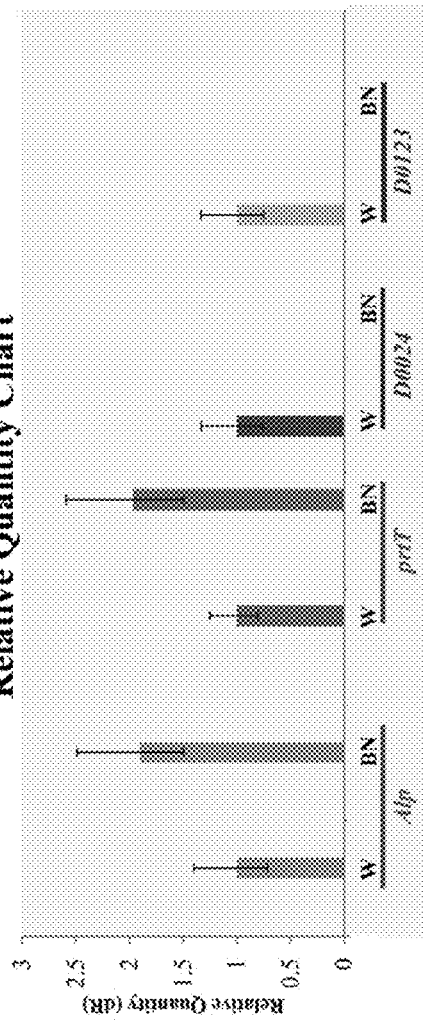
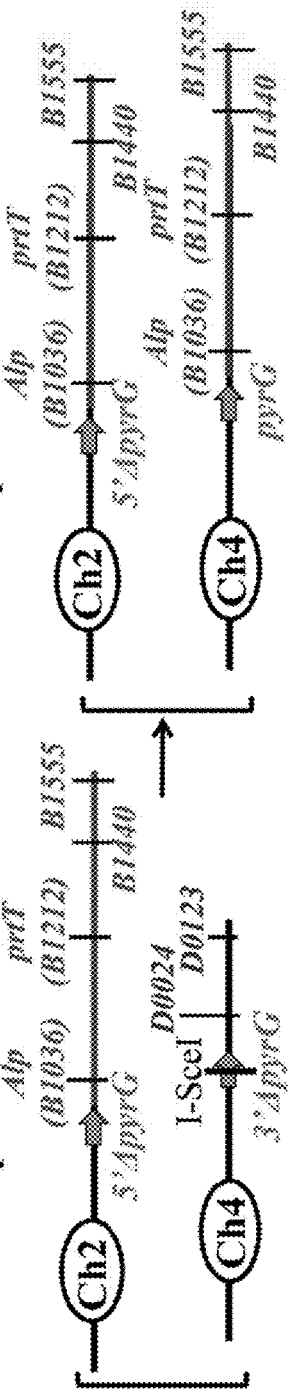
Fig. 10 Analysis of the copy number of genes by real-time PCR (1)

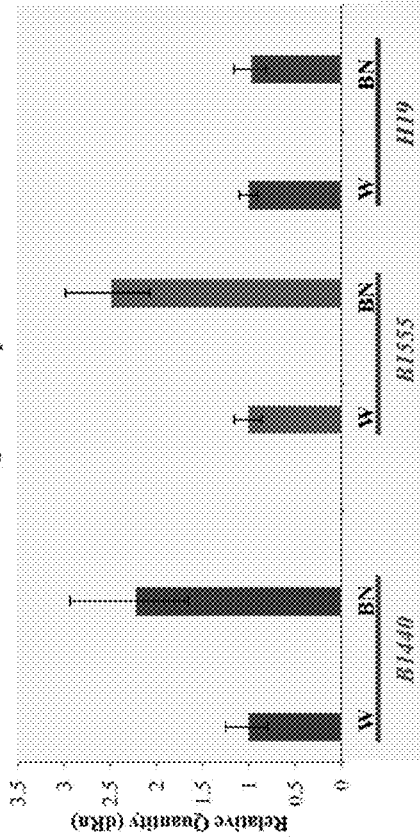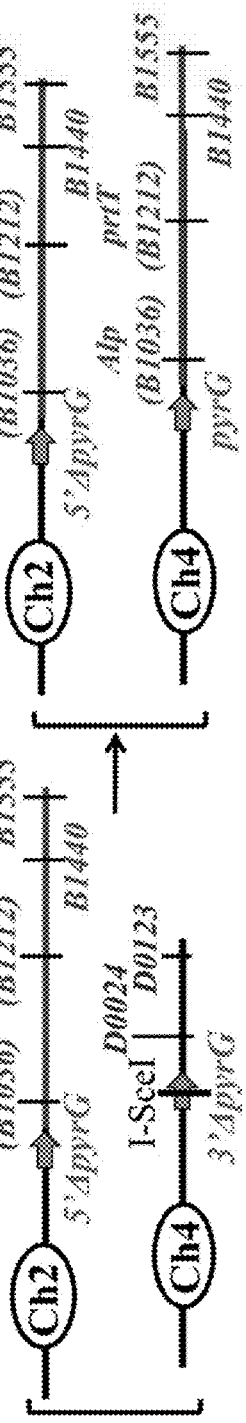
Fig. 11 Analysis of the copy number of genes by real-time PCR (2)

SEQUENCE LISTING

```
<160> NUMBER OF SEQ ID NOS: 34

<210> SEQ ID NO 1
<211> LENGTH: 24
<212> TYPE: DNA
<213> ORGANISM: Artificial Sequence
<220> FEATURE:
<223> OTHER INFORMATION: r52UR

<400> SEQUENCE: 1
agtggtcaga tgcccatcaa acgg                                             24

<210> SEQ ID NO 2
<211> LENGTH: 25
<212> TYPE: DNA
<213> ORGANISM: Artificial Sequence
<220> FEATURE:
<223> OTHER INFORMATION: r52LR

<400> SEQUENCE: 2
cgtttgcttg tgggttgtca cgtag                                            25

<210> SEQ ID NO 3
<211> LENGTH: 23
<212> TYPE: DNA
<213> ORGANISM: Artificial Sequence
<220> FEATURE:
<223> OTHER INFORMATION: Alp-U

<400> SEQUENCE: 3
ttgagcgcaa ctacaagatc aac                                              23

<210> SEQ ID NO 4
<211> LENGTH: 23
<212> TYPE: DNA
<213> ORGANISM: Artificial Seqeucne
```

```
<220> FEATURE:
<223> OTHER INFORMATION: Alp-L

<400> SEQUENCE: 4
ggtagtcagg ccatcgaggt agt                                          23

<210> SEQ ID NO 5
<211> LENGTH: 20
<212> TYPE: DNA
<213> ORGANISM: Artificial Sequence
<220> FEATURE:
<223> OTHER INFORMATION: Amy-U

<400> SEQUENCE: 5
ccacgcacat ccaactgaag                                              20

<210> SEQ ID NO 6
<211> LENGTH: 23
<212> TYPE: DNA
<213> ORGANISM: Artificial Sequence
<220> FEATURE:
<223> OTHER INFORMATION: Amy-L

<400> SEQUENCE: 6
gtcgaccacg ttgtattcct ttc                                          23

<210> SEQ ID NO 7
<211> LENGTH: 23
<212> TYPE: DNA
<213> ORGANISM: Artificial Sequence
<220> FEATURE:
<223> OTHER INFORMATION: prtT-U

<400> SEQUENCE: 7
aattcaggac ctccaatctg agt                                          23

<210> SEQ ID NO 8
<211> LENGTH: 23
<212> TYPE: DNA
<213> ORGANISM: Artificial Sequence
<220> FEATURE:
<223> OTHER INFORMATION: prtT-L

<400> SEQUENCE: 8
gatggacatg acgagtgacc ata                                          23

<210> SEQ ID NO 9
<211> LENGTH: 23
<212> TYPE: DNA
<213> ORGANISM: Artificial Sequence
<220> FEATURE:
<223> OTHER INFORMATION: 1258D-U

<400> SEQUENCE: 9
cagctttatc actttgggag ctg                                          23

<210> SEQ ID NO 10
<211> LENGTH: 24
<212> TYPE: DNA
<213> ORGANISM: Artificial Sequence
<220> FEATURE:
<223> OTHER INFORMATION: 1258D-L

<400> SEQUENCE: 10
tgagtttggc agactatagg caag                                         24
```

-continued

```
<210> SEQ ID NO 11
<211> LENGTH: 24
<212> TYPE: DNA
<213> ORGANISM: Artificial Sequence
<220> FEATURE:
<223> OTHER INFORMATION: H19-U

<400> SEQUENCE: 11
agcttgcagc cttgcacagt ccag                                              24

<210> SEQ ID NO 12
<211> LENGTH: 24
<212> TYPE: DNA
<213> ORGANISM: Artificial Sequence
<220> FEATURE:
<223> OTHER INFORMATION: H19-L

<400> SEQUENCE: 12
atggcccaca cagtgaccat cgga                                              24

<210> SEQ ID NO 13
<211> LENGTH: 24
<212> TYPE: DNA
<213> ORGANISM: Artificial Sequence
<220> FEATURE:
<223> OTHER INFORMATION: B1440U

<400> SEQUENCE: 13
aatactactc ggtcgcggat tacc                                              24

<210> SEQ ID NO 14
<211> LENGTH: 24
<212> TYPE: DNA
<213> ORGANISM: Artificial Sequence
<220> FEATURE:
<223> OTHER INFORMATION: B1440L

<400> SEQUENCE: 14
ccttctctgt aacgacgggt agac                                              24

<210> SEQ ID NO 15
<211> LENGTH: 23
<212> TYPE: DNA
<213> ORGANISM: Artificial Sequence
<220> FEATURE:
<223> OTHER INFORMATION: B1555U

<400> SEQUENCE: 15
cctacaggac gctattttca tcg                                               23

<210> SEQ ID NO 16
<211> LENGTH: 23
<212> TYPE: DNA
<213> ORGANISM: Artificial Sequence
<220> FEATURE:
<223> OTHER INFORMATION: B1555L

<400> SEQUENCE: 16
atccctgggc gacactatat ctg                                               23

<210> SEQ ID NO 17
<211> LENGTH: 23
<212> TYPE: DNA
<213> ORGANISM: Artificial Sequence
<220> FEATURE:
<223> OTHER INFORMATION: D0024U
```

<400> SEQUENCE: 17
gatacggaac aatcgctctt tcg                                         23

<210> SEQ ID NO 18
<211> LENGTH: 24
<212> TYPE: DNA
<213> ORGANISM: Artificial Sequence
<220> FEATURE:
<223> OTHER INFORMATION: D0024L

<400> SEQUENCE: 18
ctttgtagac tggaccgaaa cctg                                        24

<210> SEQ ID NO 19
<211> LENGTH: 23
<212> TYPE: DNA
<213> ORGANISM: Artificial Sequence
<220> FEATURE:
<223> OTHER INFORMATION: D0123U

<400> SEQUENCE: 19
attcctgctt acggtcgtct gtg                                         23

<210> SEQ ID NO 20
<211> LENGTH: 23
<212> TYPE: DNA
<213> ORGANISM: Artificial Sequence
<220> FEATURE:
<223> OTHER INFORMATION: D0123L

<400> SEQUENCE: 20
agtaccaacg agcccgcata tag                                         23

<210> SEQ ID NO 21
<211> LENGTH: 27
<212> TYPE: DNA
<213> ORGANISM: Artificial Sequence
<220> FEATURE:
<223> OTHER INFORMATION: B-U

<400> SEQUENCE: 21
agcaacccaa gtgcgaagcc tatcgag                                     27

<210> SEQ ID NO 22
<211> LENGTH: 26
<212> TYPE: DNA
<213> ORGANISM: Artificial Sequence
<220> FEATURE:
<223> OTHER INFORMATION: B-L

<400> SEQUENCE: 22
gaatccagtt gagtcggagc accgca                                      26

<210> SEQ ID NO 23
<211> LENGTH: 41
<212> TYPE: DNA
<213> ORGANISM: Artificial Sequence
<220> FEATURE:
<223> OTHER INFORMATION: B-iU

<400> SEQUENCE: 23
ggcagcggtt acaggtaagc tcccaatgca aacaagacaa a                     41

<210> SEQ ID NO 24

```
<211> LENGTH: 42
<212> TYPE: DNA
<213> ORGANISM: Artificial Sequence
<220> FEATURE:
<223> OTHER INFORMATION: B-iL

<400> SEQUENCE: 24
acatcacagg gtaggtccaa taaacatggc cacttttcag tt                              42

<210> SEQ ID NO 25
<211> LENGTH: 27
<212> TYPE: DNA
<213> ORGANISM: Artificial Sequence
<220> FEATURE:
<223> OTHER INFORMATION: B-OU

<400> SEQUENCE: 25
ttaaattaag gctccggaaa gacgacc                                              27

<210> SEQ ID NO 26
<211> LENGTH: 26
<212> TYPE: DNA
<213> ORGANISM: Artificial Sequence
<220> FEATURE:
<223> OTHER INFORMATION: B-OL

<400> SEQUENCE: 26
gttggcaatc gtcaaccctt aatctc                                               26

<210> SEQ ID NO 27
<211> LENGTH: 27
<212> TYPE: DNA
<213> ORGANISM: Artificial Sequence
<220> FEATURE:
<223> OTHER INFORMATION: 166-U

<400> SEQUENCE: 27
cattgagcaa tatggcgaca tcaatgg                                              27

<210> SEQ ID NO 28
<211> LENGTH: 27
<212> TYPE: DNA
<213> ORGANISM: Artificial Sequence
<220> FEATURE:
<223> OTHER INFORMATION: 166-L

<400> SEQUENCE: 28
gggctagtga agggtatgtt atacgga                                              27

<210> SEQ ID NO 29
<211> LENGTH: 28
<212> TYPE: DNA
<213> ORGANISM: Artificial Sequence
<220> FEATURE:
<223> OTHER INFORMATION: 166-OU

<400> SEQUENCE: 29
ctattgttcg gattcgcttg tagttacc                                             28

<210> SEQ ID NO 30
<211> LENGTH: 26
<212> TYPE: DNA
<213> ORGANISM: Artificial Sequence
<220> FEATURE:
<223> OTHER INFORMATION: 166-OL

<400> SEQUENCE: 30
```

-continued tttacaacgt gcaaacagca agactc                26

<210> SEQ ID NO 31
<211> LENGTH: 39
<212> TYPE: DNA
<213> ORGANISM: Artificial Sequence
<220> FEATURE:
<223> OTHER INFORMATION: 166-iU

<400> SEQUENCE: 31
ggcagcggtt acaggaggga agtgaagcag taaggaacg                39

<210> SEQ ID NO 32
<211> LENGTH: 39
<212> TYPE: DNA
<213> ORGANISM: Artificial Sequence
<220> FEATURE:
<223> OTHER INFORMATION: 166-iL

<400> SEQUENCE: 32
acatcacagg gtagggttct gcctgtagcc atagctggt                39

<210> SEQ ID NO 33
<211> LENGTH: 29
<212> TYPE: DNA
<213> ORGANISM: Artificial Sequence
<220> FEATURE:
<223> OTHER INFORMATION: pyrU

<400> SEQUENCE: 33
cctaccctgt gatgttcatc actaatgcc                29

<210> SEQ ID NO 34
<211> LENGTH: 30
<212> TYPE: DNA
<213> ORGANISM: Artificial Sequence
<220> FEATURE:
<223> OTHER INFORMATION: pyrL

<400> SEQUENCE: 34
ctgtaaccgc tgcctcattt cccacaggtt                30

METHOD FOR THE PRODUCTION OF DUPLICATION AND TRANSLOCATION OF ANY REGION IN THE CHROMOSOME OF ASPERGILLUS

TECHNICAL FIELD

The present invention relates to a technique for duplicated translocation of anoptional large region (translocation of a duplicated large region) in a chromosome of a fungus belonging to *Aspergillus* to an optional site in another chromosome of the fungus.

BACKGROUND ART

*Aspergillus* strains such as *Aspergillus sojae* and *Aspergillus oryzae* have been industrially used in the production of brewed food such as soy sauce, sake (rice wine), soybean paste, etc. With a recent determination of the whole genomic sequence of *Aspergillus oryzae* and development of an exhaustive analysis of gene expression using a micro-array, it has been expected that genetic modification of their genes, especially their chromosomal modification would increase the productivity of an enzyme and improve a growth rate of these filamentous fungi.

Unlike *Aspergillus nidulans, niger, fumigatus* and *awamori* that have a mononuclear generation, koji molds such as *Aspergillus sojae* and *Aspergillus oryzae* are always kept in a multinuclear state in their whole life cycle including in a conidium condition, and their sexual generation has not yet been observed. Their nuclear-distribution mechanism from a parent cell to a daughter cell has not yet been revealed, either. Accordingly, a mutant cannot be produced by means of mating between strains or RIP (Repeat Induced Mutation), which makes it difficult to study their genetics. As a result, the genetic analysis of *Aspergillus sojae* and *Aspergillus oryzae* has fallen behind in spite of their industrially very high utility.

As it is therefore very important from an industrial point of view to breed *Aspergillus* strains of high utility such as those having high productivity of various enzymes, methods for breeding have been vigorously developed for the above purpose. There are two prominent types of such breeding methods, i.e., mutation and genetic recombination (genetic modification) methods.

The mutation method uses various mutation treatments such as X-ray, ultraviolet ray, and heavy ion beam. Useful characteristics have been used as an index for screening strains having various enzyme activities and excellent fermentation properties. Recently, the strains having such useful characteristics have been analyzed by means of genomic information to reveal that the duplication of chromosome is important for providing the *Aspergillus* strains with such useful characteristics. An *Aspergillus* strain having duplication of such a large scale as 900 kb or more was obtained by means of mutation treatment method (Patent Literature 1). It was already reported that repeated sequences were found with a high frequency at a boundary region of the duplicated region on the chromosome by analysis of a yeast obtained by means of γ-ray radiation (Non Patent Literature 1).

However, the mechanism of such duplication of the chromosome has not yet been revealed. Accordingly, It has been just possible to accidentally obtain a strain having duplication of a region relating to an enzyme by means of conventional mutation treatments and screening based on activity of said enzyme. However, since mutation will actually occur on various sites at random on the chromosome, it has been impossible to duplicate a particular region on the chromosome of the *Aspergillus* strains. Furthermore, it is well known that back mutation or revertant (elimination of the duplicated chromosome) will occur with a high frequency due to recombination between the homologous sequences in said strain having the duplication obtained by means of the conventional mutation treatments.

On the other hand, with respect to the genetic recombination method, a method for producing a large region duplication in the *Aspergillus* chromosome has been developed (Patent Literature 2) for the duplication of an optional region in tandem in the *Aspergillus* chromosome in a wide range. According to this method, it has been possible to duplicate any large region of several tens to several hundreds kb (for example, about 200 kb~about 700 kb) in the chromosome of *Aspergillus* strains.

CITATION LIST

Patent Literature

[PTL 1] Japanese Patent No. 4469014
[PTL 2] WO2011/158623 A1

Non Patent Literature

[NPL 1] Argueso et al., (2008) Proc. Natl. Acad. Sci., USA 105:11845-11850

SUMMARY OF INVENTION

Technical Problem

Although the method according to WO2011/158623 A1 made it possible to duplicate in tandem the region over 700 kb or more, it has the following problems.

First, as the tandem-duplicated sequences are present in the same chromosome, there is a possibility that the duplicated region may be eliminated due to recombination between the homologous sequences aligning in tandem under the conditions where selective pressure due to the transformation marker is not present. Accordingly, there will be a concern about Its stability under eutrophic conditions where a particular auxotrophy dose not substantially make any sense. As a result, only limited kinds of the culture medium can be used in order to stably maintain the duplication state.

Furthermore, it is technically difficult to remove only a part of the marker in the tandem duplication strain while stably maintaining the duplication. Therefore it will be hard to increase the number of copies any more unless a new marker is used, which is different from that already integrated into the chromosome of the transformant.

Purpose of the present invention is therefore to solve the above problems, and to provide a technique to duplicate and translocate any large region in the chromosome of a fungus belonging to *Aspergillus* across a wide range, so that it will be possible to stably and systematically acquire an *Aspergillus* strain having a novel trait, which was un-acquirable by conventional techniques.

Solution to Problem

The present inventor has developed a method for the production of the duplicated translocation of an optional large region in the chromosome of a fungus belonging to *Aspergillus* over a wide range.

The present invention is therefore related to the following aspects.

1. A transformant of a fungus belonging to *Aspergillus* which is characterized by that a transformation marker gene with deficiency of a terminal part at the 5' end of its coding region is integrated into an outside of the centromere side of a target region in a chromosome of the fungus subject to duplicated translocation wherein a 5' terminal (end) of the marker gene is located in the centromere side, and a transformation marker gene with deficiency of a terminal part at the 3' end of its coding region is integrated into an outside of the centromere side of a region in another chromosome of the fungus to be replaced with the target region wherein a 5' terminal (end) of the marker gene is located in the centromere side.
2. A transformant of a fungus belonging to *Aspergillus* which is characterized by that a transformation marker gene with deficiency of a terminal part at the 3' end of its coding region is integrated into an outside of the centromere side of a target region in a chromosome of the fungus subject to duplicated translocation wherein a 3' terminal (end) of the marker gene is located in the centromere side, and a transformation marker gene with deficiency of a terminal part at the 5' end of its coding region is integrated into an outside of the centromere side of a region in another chromosome of the fungus to be replaced with the target region wherein a 3' terminal (end) of the marker gene is located in the centromere side.
3. The transformant according to Aspect 1 or 2, wherein a middle portion that is present in common in the coding region of the transformation marker genes with the deficiency of the terminal part at either the 5' or 3' end of its coding region has about 100 bp~about 2 kb sequence.
4. The transformant according to any one of Aspects 1 to 3, wherein the transformation marker gene is selected form the group consisting of pyrG, sC and niaD.
5. The transformant according to any one of Aspects 1 to 4, wherein a restriction enzyme recognition site has been introduced in advance into a homologous sequence region in the middle portion of the coding region of both or either of the transformation marker genes.
6. The transformant according to Aspect 5, wherein the restriction enzyme is selected from the group consisting of I-sceI, I-ceuI, PI-pspI and PI-sceI.
7. The transformant according to Aspect 5 or 6, wherein the restriction enzyme recognition site has been introduced by a homologous recombination.
8. The transformant according to any one of Aspects 1 to 7, wherein the fungus belonging to *Aspergillus* is *Aspergillus sojae* or *Aspergillus oryzae*.
9. A method for the production of duplicated translocation of an optional region in the chromosome of a fungus belonging to *Aspergillus*, comprising:
   (1) culturing the transformant according to any one of Aspects 1 to 8;
   (2) obtaining a fungus strain wherein the target region has been duplicated and translocated by means of a homologous recombination between two different chromosomes via a repairing mechanism after a double-strand break (cleavage) in homologous sequence regions that are present in common in the middle portion of the coding region of each of the transformation marker genes integrated into said two different chromosomes; and
   (3) selecting the fungus strain wherein the target region has been duplicated by means of a trait based on the transformation marker gene with a full length of its coding region that has been constructed due to the homologous recombination.
10. The method according to Aspect 9, wherein the transformant is in a multinuclear state.
11. The method according to Aspect 9 or 10, wherein the homologous recombination between two different chromosomes is induced by irradiation of the transformant with ultraviolet.
12. The method according to any one of Aspects 9 to 11, wherein the homologous recombination is induced by culturing the transformant under the action of a restriction enzyme.
13. A fungus belonging to *Aspergillus* having translocation of a duplicated region in its chromosome, which is obtainable by the method according to any one of Aspects 9 to 12.
14. The fungus according to Aspect 13, wherein the fungus belonging to *Aspergillus* is *Aspergillus sojae* or *Aspergillus oryzae*.
15. The fungus according to Aspect 13 or 14, wherein the duplicated and translocated region has a thousand kb or more.
16. Soy sauce produced by using the fungus belonging to *Aspergillus* according to any one of Aspects 14 to 15.

Advantageous Effects of Invention

The present invention has enabled the translocation of any duplicated large region of a thousand kb or more (for example, about 1,400 kb) such as, for example, one extending from the vicinity of centromere to the vicinity of telomere in the chromosome of *Aspergillus* strains, which is larger than that duplicated by the method according to the Patent Literature 2.

By using as the target region subject to the duplicated translocation a region of the whole arm spreading from the vicinity of centromere to the vicinity of telomere in the second chromosome of the *Aspergillus* strains where many genes encoding useful substances such as enzymes are contained, it was also confirmed that the fungus belonging to *Aspergillus* having the translocation of the duplicated region in its chromosome, which is obtained by the present method, has increased by several times its enzymatic activities such as those for protease and α-amylase.

Furthermore, since the duplicated regions are present in different chromosome with each other in the strain obtained by the present method, which has the translocation of the duplicated region, there is no risk of elimination of said duplicated regions even under the conditions where selective pressure is not present, making the duplicated translocation stable.

Furthermore, since it is possible to remove only a part of the marker in the strain having the translocation of the duplicated region in its chromosome, the same marker can be recycled so as to further increase the number of copies, theoretically up to the number of terminals of the chromosomes, i.e., 16 copies.

Furthermore, since the method according to the present invention uses only endogenous genes of a host and any exogenous gene will not remain in the resulting strain having the duplication (self-cloning stain), it is a very remarkable breeding method of microorganisms used for the production of foods such as fermentation of soy sauce, for example, *Aspergillus* strains for soy sauce.

BRIEF DESCRIPTION OF DRAWINGS

FIG. 9 shows the results of PCR showing acquisition of the strain having the translocation of the duplicated region in its chromosome due to site-specific cleavage.

FIG. 10 shows the results of the analysis (1) of the numbers of copies of each gene by means of real time PCR in the strain having the translocation of the duplicated region in its chromosome due to site-specific cleavage.

FIG. 11 shows the results of the analysis (2) of the numbers of copies of each gene by means of real time PCR in the strain having the translocation of the duplicated region in its chromosome due to site-specific cleavage.

DESCRIPTION OF EMBODIMENTS OF INVENTION

It is known that a foreign DNA will be integrated into chromosome via repairing mechanism at the time of double-strand break (DSB) of chromosomal DNA. There are two kinds of mechanisms in the repairing, that is, homologous recombination and non-homologous recombination (non-homologous end joining). The integration will occur through a region having homology with the foreign DNA in the case of the homologous recombination. On the other hand, the integration will do at a random site of the chromosome regardless of a sequence of the foreign DNA in the case of the non-homologous recombination. It is conceived that the two recombination mechanisms will function in equilibration (Ristic et al., Nucl. Acids Res. (2003) 31:5229-5237).

A series of genes belonging to a so-called "rad52 group" take an essential role in the homologous recombination, which includes rad50, 51, 52, 54, Mre11 and XRS2 (Kooistra et al. 2004). The homologous recombination mechanism has been confirmed to exist in a wide range of organisms from bacteria to eukaryotic organisms. A uvsC gene has been cloned and studied using *Aspergillus nidulans*, an experimental strain belonging to *Aspergillus*, having a mononuclear conidium (van Heemst et al., Mol. Gen. Genet (1997) 254:654-64), and it was reported that the frequency of the homologous recombination would be improved by increasing expression frequency of the above genes up to a certain level (Natsume et al. Biosci. Biotechnol. Biochem. (2004) 68:1649-1656).

On the other hand, it has been revealed that the non-homologous recombination will proceed with non-homologous end joining mechanism that is completely different form the homologous recombination mechanism. Genes such as ku70, ku80, Xrcc4, LIG4 and DNAPKcs are known to take an essential role in this recombination mechanism. It is known that Ku70 and Ku80 will act as a hetero dimmer, form a complex with a nucleotide kinase (XRCC4) and DNA Ligase IV, and promote the non-homologous end joining by joining with a DNA end at the time of cleavage of the DNA double-strand break for its repairing (Walker et al., Nature (2001) 412:607-614). The non-homologous recombination via ku gene has been recognized only in eukaryotic organisms.

An outline of the production of a fungus belonging to *Aspergillus* having the translocation of the duplicated region in its chromosome will be described below.

Although it is thought that the duplication of chromosome will occur via repairing mechanism of double-strand break (DSB) made in the chromosome, its detailed mechanism has not yet been revealed. However, It was already reported that repeated sequences were found with a high frequency at a boundary region of the duplicated or translocated region in the chromosome by analysis of a diploid yeast mutant obtained by means of gamma-ray irradiation (Non Patent Literature 1).

Figure 1:
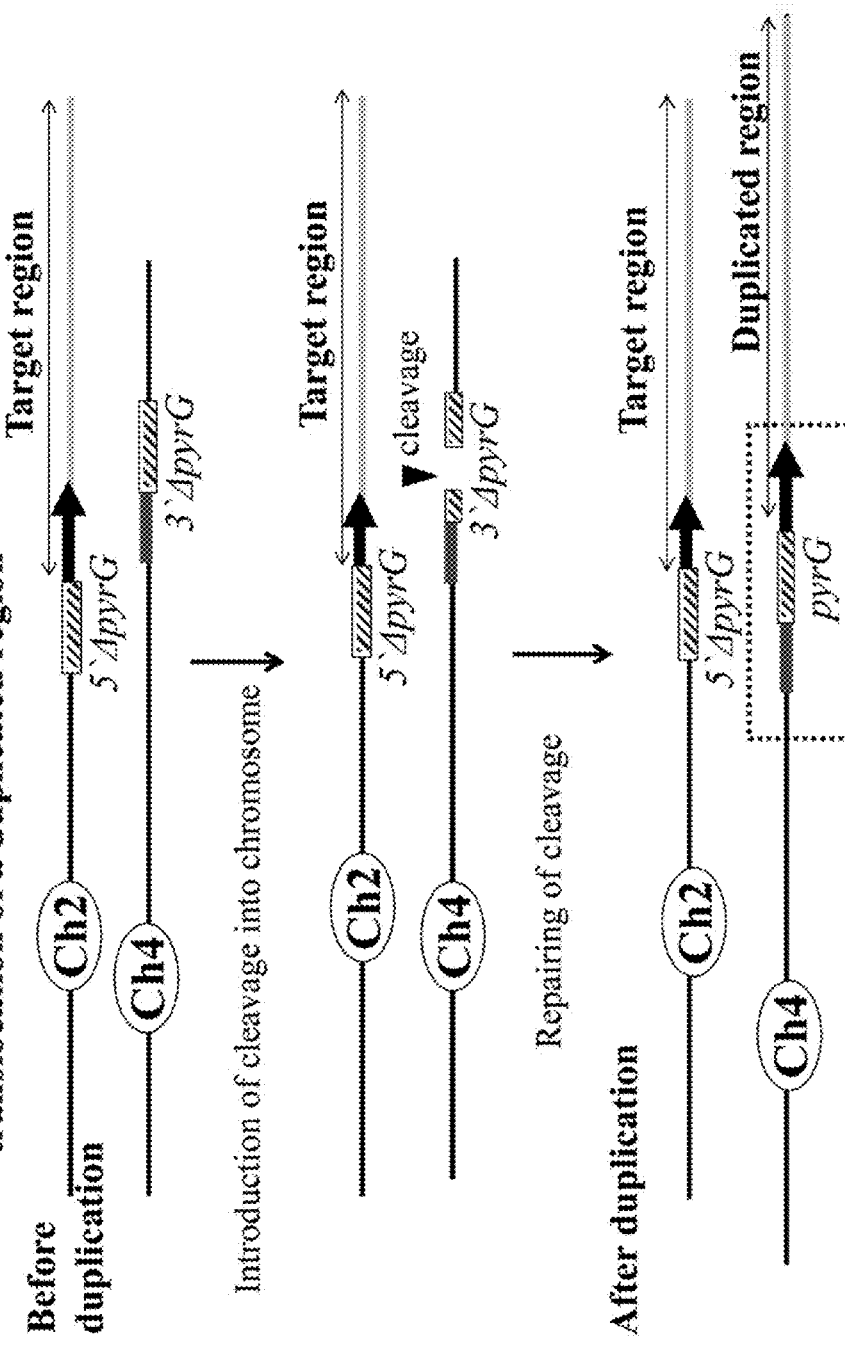
FIG. 1 is a schematic figure showing the method of the present invention.

Accordingly, it was conceived that the strains having translocation of the duplicated region at a target site in its chromosome could be obtained by producing a transformant wherein 5' ΔpyrG that has lost its genetic function due to the deficiency of a terminal part at the 5' end of its coding region was integrated into a target region in an original chromosome of the fungus subject to duplicated translocation, and 3'ΔpyrG that has lost its genetic function due to the deficiency of a terminal part at the 3' end of its coding region was integrated into a boundary region in another chromosome of the fungus to which the target region is to be translocated; and selecting during the culture of the transformant a strain wherein the whole ΔpyrG had been reconstituted due to the translocation into said desired site by means of a homologous recombination via a repairing mechanism after a double-strand break (cleavage) in the homologous sequence regions, that is, a strain that has accordingly become possible to grow in a minimum medium (FIG. 1)

The fungus belonging to *Aspergillus* that is used as a parent strain of the transformant according to the present invention includes any strains such as that of *Aspergillus sojae, Aspergillus oryzae, Aspergillus niger, Aspergillus awamori* and the like, strains of *Aspergillus sojae* and *Aspergillus oryzae* being preferable.

Their specific strains include, for example, those deposited at a public depository institution and easily available to those skilled in the art such as *Aspergillus sojae* 262 (FERM P-2188), *Aspergillus sojae* 2165 (FERM P-7280), *Aspergillus sojae* (ATCC 42251), *Aspergillus oryzae* (IAM2638) and *Aspergillus oryzae* RIB40 (NBRC100959).

It is now possible to perform the duplicated translocation of any large region of a thousand kb or more in the chromosome of *Aspergillus* strains.

Thus, in a first type of the transformant of the fungus belonging to *Aspergillus* according to the present invention, a transformation marker gene with deficiency of a terminal part at the 5' end of its coding region is integrated into an outside of a target region in a chromosome of the fungus subject to duplicated translocation, and a transformation marker gene with deficiency of a terminal part at the 3' end of its coding region is integrated into an outside of a region in another chromosome of the fungus to be replaced with the target region.

More specifically, in the first type, the transformation marker gene with deficiency of the terminal part at the 5' end of its coding region is integrated into an outside of the centromere side of the target region in a chromosome of the fungus subject to duplicated translocation wherein a 5' terminal (end) of the marker gene is located in the centromere side, and the transformation marker gene with deficiency of the terminal part at the 3' end of its coding region is integrated into an outside of the centromere side of the region in another chromosome of the fungus to be replaced with the target region wherein a 5' terminal (end) of the marker gene is located in the centromere side.

On the other hand, in a second type of the transformant of the fungus belonging to *Aspergillus* according to the present invention, a transformation marker gene with deficiency of a terminal part at the 3' end of its coding region is integrated into an outside of a target region in a chromosome of the fungus subject to duplicated translocation, and a transformation marker gene with deficiency of a terminal part at the 5' end of its coding region is integrated into an outside of a region in another chromosome of the fungus to be replaced with the target region.

More specifically, in the second type, the transformation marker gene with deficiency of the terminal part at the 3' end of its coding region is integrated into an outside of the centromere side of the target region in a chromosome of the fungus subject to duplicated translocation wherein a 3' terminal (end) of the marker gene is located in the centromere side, and the transformation marker gene with deficiency of the terminal part at the 5' end of its coding region is integrated into an outside of the centromere side of the region in another chromosome of the fungus to be replaced with the target region wherein a 3' terminal (end) of the marker gene is located in the centromere side.

Both in the first and second types of the transformant, the target region subject to the duplicated translocation in a chromosome may be located in either a long arm side or a short arm side. Similarly, the region in another chromosome to be replaced with the target region may be located in either a long arm side or a short arm side. In the present specification, a telomere terminal in the short arm is defined as an "upstream side", and a telomere terminal of the long arm is defined as a "downstream side." As a result, the following four examples are feasible depending on whether the target region subject to duplicated translocation and the region in another chromosome to be replaced with the target region may be located in the long arm or in the short arm, respectively.

Thus, the first type of the transformant according to the present invention will have the following four examples.

In the first example wherein both the target region subject to the duplicated translocation and the region in another chromosome to be replaced with the target region are located in each long arm, the transformation marker gene with deficiency of the terminal part at the 5' end of its coding region is integrated into the outside of a 5' terminal of the target region in a chromosome of the fungus subject to the duplicated translocation wherein a 5' side of the marker gene is located in the upstream side, and the transformation marker gene with deficiency of the terminal part at the 3' end of its coding region is integrated into an outside of a 5' terminal of the region in another chromosome of the fungus to be replaced with the target region wherein a 5' side of the marker gene is located in the upstream side.

In the second example wherein both the target region subject to the duplicated translocation and the region in another chromosome to be replaced with the target region are located in each short arm, the transformation marker gene with deficiency of the terminal part at the 5' end of its coding region is integrated in a reversed direction into the outside of a 3' terminal of the target region in a chromosome of the fungus subject to the duplicated translocation wherein an 3' side of the marker gene is located in the upstream side, and the transformation marker gene with deficiency of the terminal part at the 3' end of its coding region is integrated in a reversed direction into an outside of a 3' terminal of the region in another chromosome of the fungus to be replaced with the target region wherein an 3' side of the marker gene is located in the upstream side.

In the third example wherein the target region subject to the duplicated translocation and the region in another chromosome to be replaced with the target region are located in the long arm and in the short arm, respectively, the transformation marker gene with deficiency of the terminal part at the 5' end of its coding region is integrated into the outside of the 5' terminal of the target region in a chromosome of the fungus subject to the duplicated translocation wherein the 5' side of the marker gene is located in the upstream side, and the transformation marker gene with deficiency of the terminal part at the 3' end of its coding region is integrated in a reversed direction into an outside of the 3' terminal of the region in another chromosome of the fungus to be replaced with the target region wherein the 3' side of the marker gene is located in the upstream side.

In the forth example wherein the target region subject to the duplicated translocation and the region in another chromosome to be replaced with the target region are located in the short arm and in the long arm, respectively, the transformation marker gene with deficiency of the terminal part at the 5' end of its coding region is integrated in a reversed direction into the outside of the 3' terminal of the target region in a chromosome of the fungus subject to the duplicated translocation wherein the 3' side of the marker gene is located in the upstream side, and the transformation marker gene with deficiency of the terminal part at the 3' end of its coding region is integrated into an outside of the 5' terminal of the region in another chromosome of the fungus to be replaced with the target region wherein the 5' side of the marker gene is located in the upstream side.

Similarly, the second type of the transformant according to the present invention will also have the following four examples.

In the first example wherein both the target region subject to the duplicated translocation and the region in another chromosome to be replaced with the target region are located in each long arm, the transformation marker gene with deficiency of the terminal part at the 3' end of its coding region is integrated in a reversed direction into the outside of the 5' terminal of the target region in a chromosome of the fungus subject to the duplicated translocation wherein the 3' side of the marker gene is located in the upstream side, and the transformation marker gene with deficiency of the terminal part at the 5' end of its coding region is integrated in a reversed direction into the outside of the 5' terminal of the region in another chromosome of the fungus to be replaced with the target region wherein the 3' side of the marker gene is located in the upstream side.

In the second example wherein both the target region subject to the duplicated translocation and the region in another chromosome to be replaced with the target region are located in each short arm, the transformation marker gene with deficiency of the terminal part at the 3' end of its coding region is integrated into the outside of the 3' terminal of the target region in a chromosome of the fungus subject to the duplicated translocation wherein the 5' side of the marker gene is located in the upstream side, and the transformation marker gene with deficiency of the terminal part at the 5' end of its coding region is integrated into an outside of the 3' terminal of the region in another chromosome of the fungus to be replaced with the target region wherein the 5' side of the marker gene is located in the upstream side.

In the third example wherein the target region subject to the duplicated translocation and the region in another chromosome to be replaced with the target region are located in the long arm and in the short arm, respectively, the transformation marker gene with deficiency of the terminal part at the 3' end of its coding region is integrated in a reversed direction into the outside of the 5' terminal of the target region in a chromosome of the fungus subject to the duplicated translocation wherein the 3' side of the marker gene is located in the upstream side, and the transformation marker gene with deficiency of the terminal part at the 5' end of its coding region is integrated into an outside of the 3' terminal of the region in another chromosome of the fungus to be replaced with the target region wherein the 5' side of the marker gene is located in the upstream side.

In the forth example wherein the target region subject to the duplicated translocation and the region in another chromosome to be replaced with the target region are located in the short arm and in the long arm, respectively, the transformation marker gene with deficiency of the terminal part at the 3' end of its coding region is integrated into the outside of the 3' terminal of the target region in a chromosome of the fungus subject to the duplicated translocation wherein the 5' side of the marker gene is located in the upstream side, and the transformation marker gene with deficiency of the terminal part at the 5' end of its coding region is integrated in a reversed direction into an outside of the 5' terminal of the region in another chromosome of the fungus to be replaced with the target region wherein the 3' side of the marker gene is located in the upstream side.

By culturing the transformant having the above structural features, it is possible to obtain the fungus strain wherein the target region has been duplicated and translocated by means of the homologous recombination between two different chromosomes via a repairing mechanism after the double-strand break in the homologous sequence regions (a shaded area in FIGS. 1 and 2) that are present in common in the middle portion of the coding region of each of the transformation marker genes integrated into said two different chromosomes. The target region and the two different chromosomes may be optionally selected depending on the kinds of said region and strains. For example, as described in the Examples of the present specification, the whole arm spreading from the vicinity of centromere to the vicinity of telomere in the second chromosome of the *Aspergillus* strains where many genes encoding useful substances such as enzymes are contained may be selected as the target region.

In the examples where both the target region subject to the duplicated translocation and the region in another chromosome to be replaced with the target region are located in the same side, i.e., either in the long arm or in the short arm, the target region subjected to the duplicated translocation will be integrated so that its 5' side is located in the upstream side in the resulting strain having translocation of the duplicated region by means of the homologous recombination.

On the other hand, in the examples where the target region subject to duplicated translocation is located either in the long arm or in the short arm, and the region in another chromosome to be replaced with the target region is located in the other arm, the target region subjected to the duplicated translocation will be integrated in a reversed direction so that its 3' side is located in the upstream side in the resulting strain having translocation of the duplicated region by means of the homologous recombination.

It may be advantageous that a transformant wherein a gene involved in the non-homologous recombination is deleted or suppressed (Japanese Patent Publication 2006-158269) is used as the fungus belonging to *Aspergillus* according to the present invention.

It is preferred that the transformation marker gene integrated into the transformant has deficiency in its terminal part at either the 5' or 3' end of its coding region, so that it will leave a base sequence long enough to efficiently generate homologous recombination, for example, a base (nucleotide) sequence with several hundreds by or more, several hundreds by to several kb (e.g., about 100 bp to about 2 kb) in the middle portion of the coding region of the transformation marker gene. In other words, it is preferred that the base sequence with said length is kept in the middle portion of the coding region of the original transformation marker gene in both of the transformation marker genes integrated into the two different chromosomes. Accordingly, the length of base sequence to be deleted in its terminal part at the 5' or 3' end of the coding region of the original transformation marker gene may be optionally determined by those skilled in the art depending on a kind, full length and the like of the transformation marker gene to be used. For example, said length may be usually about 0.4 kb~about 1.4 kb in the case of pyrG gene. Additionally, it is not necessary for both of the base sequences to be deleted in the terminal part at the 5' and 3' ends to have the same length to each other.

During the culture of the transformant according to the present invention, the full length of the coding region of the transformation marker gene has been constructed due to the homologous recombination in a fungus strain simultaneously as the target region has been duplicated and translocated. As a result, such strain can be selected or distinguished by means of the trait based on the transformation marker gene from a fungus strain wherein the target region is not duplicated, i.e., the full length of the coding region of the transformation marker gene is not constructed. By the way transcription-regulating regions such as promoter region and terminator region may be also contained in the 5' side of the coding region of the transformation marker gene.

Although there is no limitation in the transformation marker gene to be used in the present invention, pyrG sC and niaD may be exemplified as a positive selection marker gene, which will enable the selection of the fungus strain wherein the target region has been duplicated and translocated by means of a trait that can compensate various kinds of auxotrophy such as uridine requirement, sulfur assimilation and nitric assimilation.

These marker genes may be also used for a negative selection wherein a strain is cultured in a culture medium comprising a drug for selection so that a cytotoxic substance that has been converted from the drug by an expressed product of said genes will kill the strain.

Furthermore, a restriction enzyme recognition site for an appropriate restriction enzyme known in the art such as I-sceI, I-ceuI, PI-pspI and PI-sceI may be introduced in advance into a homologous sequence region in the middle portion of the coding region of both or either of the transformation marker genes. The above restriction enzyme recognition site may be introduced by any means known for those skilled in the art such as homologous recombination method.

Thus, the present invention is also related to a method for the production of duplicated translocation of an optional region in the chromosome of a fungus belonging to *Aspergillus* by using the above transformant, which is outlined in FIG. 1. Thus, the method comprises:

(1) culturing the transformant according to any one of Aspects 1 to 8;

(2) obtaining a fungus strain wherein the target region has been duplicated and translocated by means of a homologous recombination between two different chromosomes via a repairing mechanism after a double-strand break in homologous sequence regions that are present in common in the middle portion of the coding region of each of the transformation marker genes integrated into said two different chromosomes; and (3) selecting the fungus strain wherein the target region has been duplicated by means of a trait based on the transformation marker gene with a full length of its coding region that has been constructed due to the homologous recombination.

The above method utilizes the homologous recombination via the repairing mechanism that will function when the double-strand break in the homologous sequence regions that are present in common in the middle portion of the coding region of the transformation marker genes occurs with an appropriate frequency during the culture of said transformant under usual conditions.

It is possible to promote the homologous recombination between the two different chromosome so as to increase its efficiency by performing an appropriate mutation treatment known in the art such as irradiation with ultraviolet or X-ray on the conidium of the transformant before the initiation of its culture. For example, ultraviolet irradiation may be carried out to the conidium suspension by any method known for those skilled in the art, usually by means of 15 W ultraviolet lamp for 1-10 min. It is not necessary to bring the transformant into a protoplast state in the culture according to the present method.

Furthermore, the homologous recombination may be induced by culturing the transformant under the action of an appropriate restriction enzyme known in the art such as I-sceI, I-ceuI, PI-pspI and PI-sceI in the case where the recognition site for the restriction enzyme has been introduced in advance into the transformation marker genes. Specifically, the transformant in the protoplast state may be mixed with the restriction enzyme in the presence of a fusion auxiliary agent such as PEG so as to make the restriction enzyme efficiently affect the transformant (protoplast PEG method).

The transformant according to the present invention may be constructed by any method known for those skilled in the art such as those described in the present specification. It may be cultured under appropriate conditions known in the art.

The present invention also relates to a fungus belonging to *Aspergillus* having the translocation of a duplicated region with a thousand or more kb (for example, about 1,400 kb) in its chromosome, which is obtained by the method according to method according to the present invention. Since the target region subject to the duplicated translocation may be optionally selected, it is possible to obtain *Aspergillus* strains that are useful in the production of foods such as fermentation of soy sauce (for example, *Aspergillus* strains for soy sauce). The present invention is therefore related to foods such as soy sauce produced by using said fungus belonging to *Aspergillus*.

The present invention will be specifically explained below with reference to the examples, which should not be construed to limit the scope of the present invention.

Experimental Methods

Strains

*Aspergillus oryzae* RP-1 strain (ΔpyrG) was used, which was a pyrG deletion strain (Takahashi et al. (2006) Biosci. Biotechnol. Biochem. 70:135-143) prepared from RIB40 strain (ATCC42149).

Culture Medium:

Polypeptone dextrin (PD) medium (polypepton 1%, dextrin 2%, $KH_2PO_4$ 0.5° A, $NaNO_3$ 0.1%, $MgSO_4$ 0.05%, casamino acid 0.1%, pH 6.0), CzapekDox (CZ) minimum medium, and 1.2M sorbitol CZ (as regeneration medium) were used. CZ medium containing 1.5 mg/ml 5-fluoroortic acid (5FOA: Sigma Co.) and 20 mM Uridine was used as a medium for positive selection of a pyrG⁻ (Uridine-auxotrophy) strain.

Transformation:

Conidium was inoculated on liquid PD medium (50 ml) containing 20 mM Uridine in a conical flask (150 ml) and subjected to shake culture for about 20 hours at 30° C., followed by collection of mycelium. The collected mycelium was washed with 0.7M KCl buffer, shaken gently in 0.7M KCl buffer containing 1% Lysing enzyme (Sigma Co.) for 3 hours at 30° C. to prepare protoplast. The resulting protoplast was washed with 1.2M sorbitol buffer, and transformed by means of a protoplast PEG method. Regeneration of the resulting transformant was carried out on 1.2M sorbitol CZ medium containing 0.5% agar.

Construction of a Strain Having the Translocation of the Duplicated Region Using I-secI A strain having the duplicated translocation was prepared as follows. PEG solution (20 µl) and I-secI (50 U or 0 U) were added to protoplast solution of about $2 \times 10^7/100$ µl, which was then kept on ice for 40 min., mixed again with PEG solution (70 µl) and kept at a room temperature for 20 min., followed by regeneration on 1.2M sorbitol CZ medium plate. The strains that could grow were used as a candidate for the strains having the duplicated translocation in the following analysis.

Preparation of Wheat-Bran Koji Mold (*Aspergillus* Strain)

The enzyme activity of *Aspergillus* strain was carried out in a conventional manner. Thus, wheat bran with sprayed to 80% water (5 g) was placed into a conical flask (150 ml) and sterilized for 50 min. at 121° C. To this was inoculated two platinum loops of the *Aspergillus* strain and cultured for 4 days at 30° C. The culture was then mixed with 100 ml of sterilized water, sealed with a rubber plug, sufficiently shaken, allowed to stand for 4 hours at a room temperature and filtered with paper filter No. 2 (Advantech Co.) to give an extract solution, which was used as an enzyme sample.

Determination of Protease Activity

The resulting enzyme sample was appropriately diluted, and determined by a method described in "Soy sauce test method" (Japan Soysauce Institute, Showa 60 (1985), p. 287). The protease activity was indicated with a titer of "1 U" that could generate 1 µmol of tyrosine for one minute per 1 g of wheat bran koji mold.

Determination of α-Amylase Activity

The resulting enzyme sample was appropriately diluted, and subjected to determination with α-amylase determination kit (Kikkoman brewing analysis kit, code 60213) in accordance with a protocol of the kit. The α-amylase activity was shown with a titer of "1 U" that could release 1 µmol of 2-chrolo-4-nitrophenol for one minute per 1 g of wheat bran koji mold.

Comparison of the Number of Gene Copies in the Chromosome by Means of Quantitative PCR (Real-Time PCR)

The quantitative PCR was carried out using Mx3005P (Agilent Technologies). The numbers of copies of Alp (B1036), amyR, prtT (81212), D1258, 81440, B1555 on the $2^{nd}$ chromosome, D0024 and D0123 on the 4th chromosome, and H19 on the $8^{th}$ chromosome were compared between the parent strain (RIB40) and the strains having the duplicated translocation (UV4-C strain and BN1-1 strain) by means of a relatively quantitative method with rad52 as a mormalizer. The PCR was first kept for ten min, at 95° C., followed by repeating 40 times a cycle of heating for 20 seconds at 95° C., for 30 seconds at 58° C. and for 30 seconds at 72° C. The genes of rad52, Alp, prtT, H19, D1258, 81440, 81555, D0024 and D0123 were amplified using the primers of r52UR-r52LR, AlpU-AlpL, prtTU-prtTL, H19 U-H19L, 1258D U-1258D L, B1440 U-B1440L, B1555 U-B1555L, D0024 U-D0024L and D0123 U-D0123L, respectively (Table 1).

TABLE 1

Sequences of primers used in peal-time PCR

| primer | sequence (5'-3') | SEQ ID NO |
|---|---|---|
| r52UR | AGTGGTCAGATGCCCATCAAACGG | 1 |
| r52LR | CGTTTGCTTGTGGGTTGTCACGTAG | 2 |
| Alp-U | TTGAGCGCAACTACAAGATCAAC | 3 |
| Alp-L | GGTAGTCAGGCCATCGAGGTAGT | 4 |
| Amy-U | CCACGCACATCCAACTGAAG | 5 |
| Amy-L | GTCGACCACGTTGTATTCCTTTC | 6 |
| prtT-U | AATTCAGGACCTCCAATCTGAGT | 7 |
| prtT-L | GATGGACATGACGAGTGACCATA | 8 |
| 1258D-U | CAGCTTTATCACTTTGGGAGCTG | 9 |
| 1258D-L | TGAGTTTGGCAGACTATAGGCAAG | 10 |
| H19-U | AGCTTGCAGCCTTGCACAGTCCAG | 11 |
| H19-L | ATGGCCCACACAGTGACCATCGGA | 12 |
| B1440U | AATACTACTCGGTCGCGGATTACC | 13 |
| B1440L | CCTTCTCTGTAACGACGGGTAGAC | 14 |
| B1555U | CCTACAGGACGCTATTTTCATCG | 15 |
| B1555L | ATCCCTGGGCGACACTATATCTG | 16 |
| D0024U | GATACGGAACAATCGCTCTTTCG | 17 |
| D0024L | CTTTGTAGACTGGACCGAAACCTG | 18 |
| D0123U | ATTCCTGCTTACGGTCGTCTGTG | 19 |
| D0123L | AGTACCAACGAGCCCGCATATAG | 20 |

Table 2 shows the sequences of primers used in the construction of the vector for the production of the strain having the duplicated translocation, and confirmation of said strain.

TABLE 2

Sequences of primers used in the production of the strain having the duplication

| primer | sequence (5'-3') | SEQ ID NO |
|---|---|---|
| B-U | AGCAACCCAAGTGCGAAGCCTATCGAG | 21 |
| B-L | GAATCCAGTTGAGTCGGAGCACCGCA | 22 |
| B-iU | GGCAGCGGTTACAGGTAAGCTCCCAATGCAA ACAAGACAAA | 23 |
| B-iL | ACATCACAGGGTAGGTCCAATAAACATGGCC ACTTTTCAGTT | 24 |
| B-OU | TTAAATTAAGGCTCCGGAAAGACGACC | 25 |
| B-OL | GTTGGCAATCGTCAACCCTTAATCTC | 26 |
| 166-U | CATTGAGCAATATGGCGACATCAATGG | 27 |
| 166-L | GGGCTAGTGAAGGGTATGTTATACGGA | 28 |
| 166-OU | CTATTGTTCGGATTCGCTTGTAGTTACC | 29 |
| 166-OL | TTTACAACGTGCAAACAGCAAGACTC | 30 |
| 166-iU | GGCAGCGGTTACAGGAGGGAAGTGAAGCAGTA AGGAACG | 31 |
| 166-iL | ACATCACAGGGTAGGGTTCTGCCTGTAGCCAT AGCTGGT | 32 |
| pyrU | CCTACCCTGTGATGTTCATCACTAATGCC | 33 |
| pyrL | CTGTAACCGCTGCCTCATTTCCCACAGGTT | 34 |

Example 1

Production of the Strains Having the Translocation of the Duplicated Region in its Chromosome Due to Ultraviolet Irradiation

[Construction of the Transformant]

Figure 3:
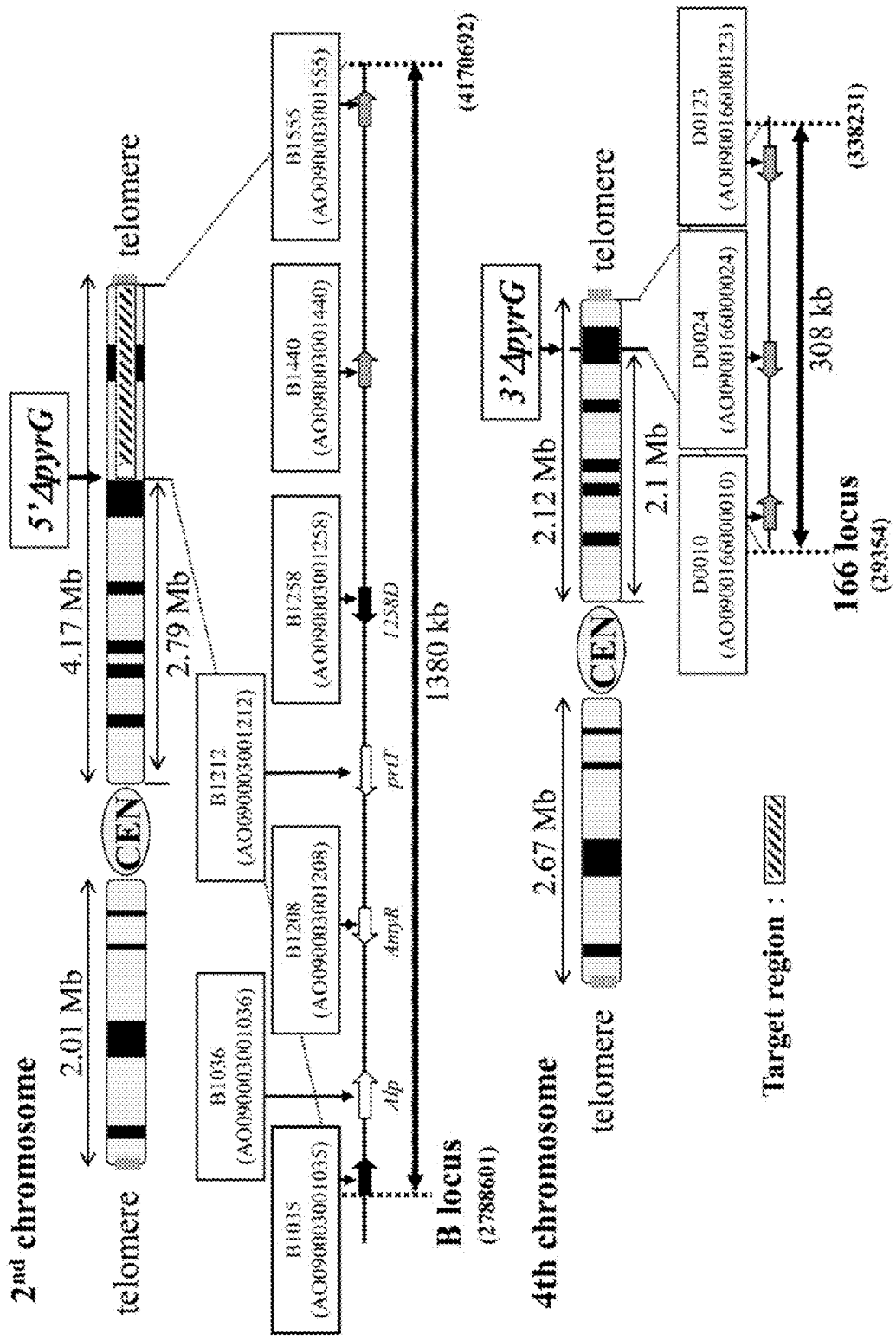
FIG. 3 shows a target region before the duplicated translocation.

The region subject to the duplicated translocation was a 1,380 kb region comprising a part corresponding to the ORF regions of A0090003001035~A0090003001556 in SC003 region of the 2nd chromosome of Aspergillus oryzae (a shaded area in FIG. 3). This region was duplicated and translocated to the telomere side of a boundary region between A0090166000009~A0090166000010 (166 locus) in SC166 region of the 4th chromosome. Vectors for integrating 5' DpyrG into the B locus and 3' DpyrG into the 166 locus, respectively were constructed for the above purpose. Just for the purpose of simplification, the part of "A0090003000" of each gene is hereinafter abbreviated just to "B." Thus, for example, "A0090003000160" is abbreviated into "B0160." Similarly, the part of "A0090166000" of each gene is hereinafter abbreviated just to "D." Thus, for example, "A00901660000010" is abbreviated into "D0010." The SC003 and SC166 regions and sequences of the genes contained therein were based on the genome analysis database of National Institute of Technology and Evaluation (NITE), DOGAN (Database Of the Genomes Analyzed at NITE) (www.bio.nite.go.jp/dogan/GeneMap?GENOME_ID=ao_G2).

Figure 4:
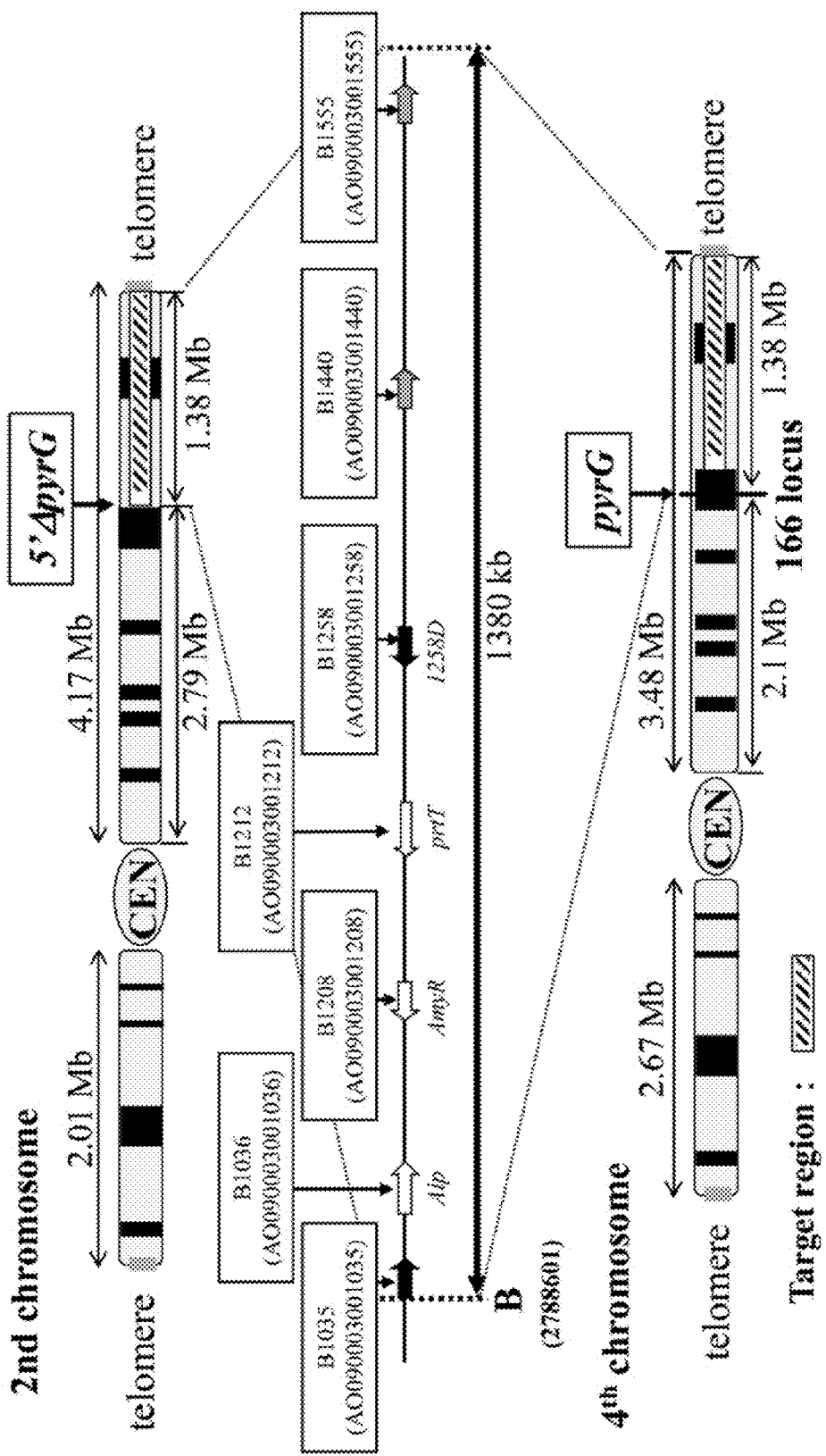
FIG. 4 shows a target region after the duplicated translocation.

As expected, the duplicated region in the $2^{nd}$ chromosome was translocated into the $4^{th}$ chromosome to give a strain having the chromosomal structure shown in FIG. 4

Preparation of the 5' ΔpyrG and 3' ΔpyrG

Figure 2:
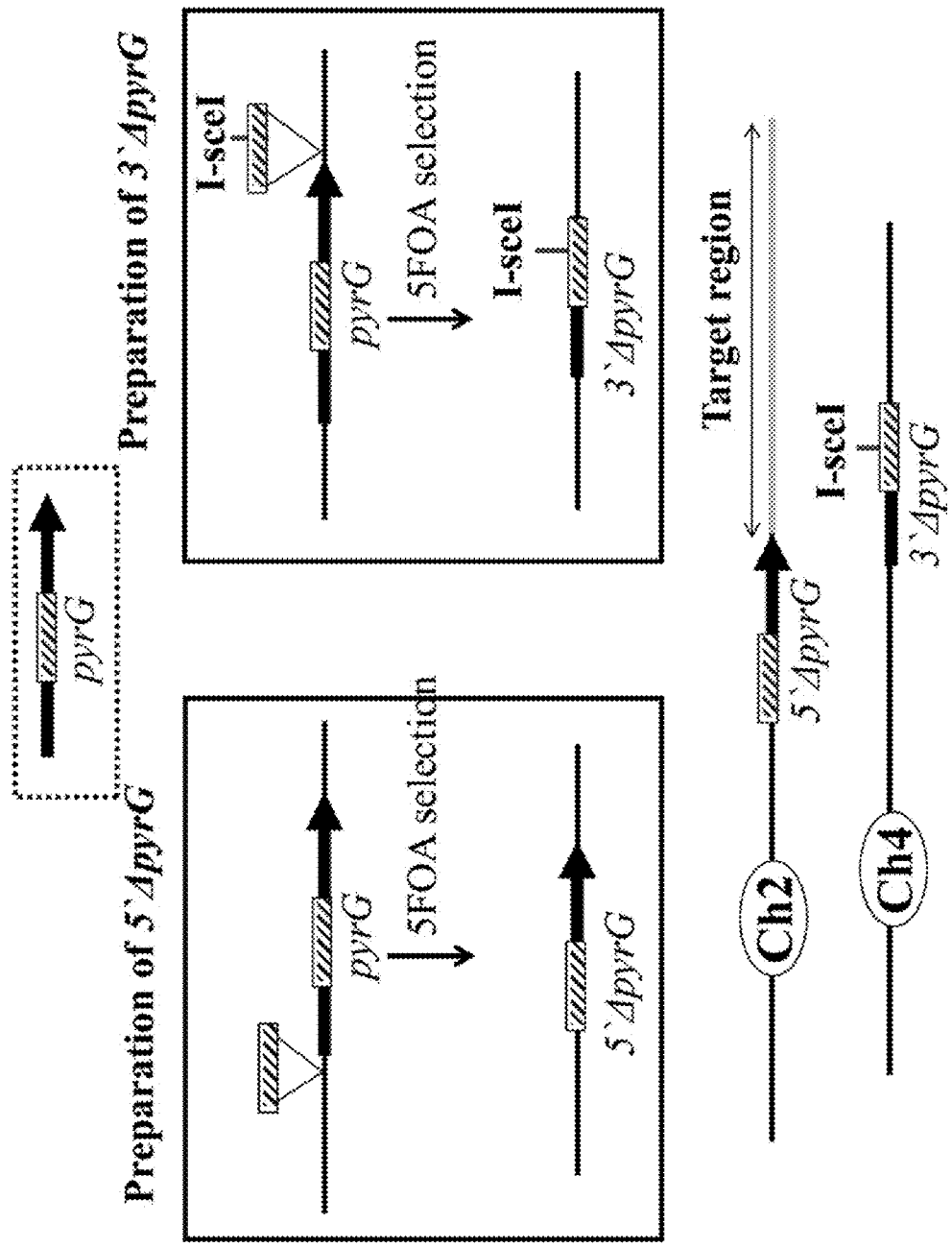
FIG. 2 shows a preparation of 5' ΔpyrG or 3' ΔpyrG unit.

First, a basic unit shown in FIG. 2 was first made for preparing the 5' ΔpyrG and 3' ΔpyrG. The 5' ΔpyrG and 3' ΔpyrG units were prepared by means of PCR and ligation. The preparation of these ΔpyrG units was carried out by inserting the homologous sequence shown with hatched lines in FIG. 2, which may comprise the recognition site for an appropriate restriction enzyme, around an transcription initiation point of the full length of pyrG (5' ΔpyrG) or around the 3' of the coding region (3' ΔpyrG). After each of these vectors had been integrated into the chromosome, selection of a 5FOA-resistant strain (negative selection) was made to give a strain comprising the 5' ΔpyrG or 3' ΔpyrG unit wherein an internal part has been excised due to the recombination within the homologous region.

Construction of a Vector for Integrating the 5' ΔpyrG Unit into the B Locus in the $2^{nd}$ Chromosome Vectors for the integration of the 5' ΔpyrG and 3' ΔpyrG units, respectively, to a desired region in each chromosome were constructed.

First, the vector for integrating 5' ΔpyrG unit into the B locus in the $2^{nd}$ chromosome was constructed as follows.

A DNA fragment of 3 kb comprising a part adjacent to the B locus was obtained with PCR using the primers B-U and B-L and the genomic DNA of *Aspergillus oryzae* RIB40 strain as a template. The resulting fragment was purified and subjected to a cloning by means of TOPO-TA cloning kit (invitrogen). A DNA fragment of about 6 kb was then prepared by amplification using the primers B-iU and B-iL, and the resulting plasmid as a template. The 5' ΔpyrG unit was then amplified using the primers P-U and P-L to give a fragment of about 3 kb. These fragments were purified and treated by In-fusion cloning kit (Takara) to give a vector pB-d5pyrG.

Construction of a Vector for Integrating the 3' ΔpyrG Unit into the 166 Locus in the 4th Chromosome Then, the vector for integrating 3' ΔpyrG unit into the 166 locus in the $4^{th}$ chromosome was constructed as follows.

A DNA fragment of 3 kb comprising a part adjacent to the B locus was obtained with PCR using the primers 166-U and 166-L and the genomic DNA of *Aspergillus oryzae* RIB40 strain as a template. The resulting fragment was purified and subjected to a cloning by means of TOPO-TA cloning kit (invitrogen). A DNA fragment of about 6 kb was then prepared by amplification using the primers 166-iU and 166-iL, and the resulting plasmid as a template. The 3' ΔpyrG unit was then amplified using the primers P-U and P-L to give a fragment of about 3 kb. These fragments were purified and treated by In-fusion cloning kit (Takara) to give a vector p166-d3pyrG.

Construction of a Parent Strain for the Duplicated Translocation

The resulting vectors were integrated into the B-locus and 166-locus of *Aspergillus oryzae*, respectively, to give a transformant for the duplicated translocation.

First, *Aspergillus oryzae* RP-1 strain (ΔpyrG) was transformed with a fragment obtained by the amplification of the vector pB-d5pyrG with the primers B-U and B-L. The transformants grown on the regeneration medium was screened with the primers B-OU and B-OL to obtain a strain comprising the vector integrated into the B-locus. Conidium was collected from the strain and applied on the CZ medium plate containing 5FOA. After culture for about one week at 30° C., DNA was extracted from a resistant strain having produced a lot of adhering conidium and subjected to PCR using the primers B-OU and B-OL to confirm the deficiency of the terminal part at the 5' end of pyrG so that the strain could not grow in the minimum medium. A strain having the 5' ΔpyrG integrated into the B-locus (AO-B-d5pyrG strain) was thus obtained. Then, the resulting AO-B-d5pyrG strain was transformed with a fragment obtained by the amplification of the vector p166-d3pyrG with the primers 166-U and 166-L. The transformants regenerated on the minimum medium was screened with the primers 166-OU and 166-OL to obtain a strain comprising the vector integrated into the 166-locus. Conidium was collected from the strain and applied on the CZ medium plate containing 5FOA. After culture for about one week at 30° C., DNA was extracted from a resistant strain having produced a lot of adhering conidium and subjected to PCR using the primers 166-OU and 166-OL to confirm the deficiency of the terminal part at the 3' end of pyrG so that the strain could not grow in the minimum medium. Thus, a transformant according to the present invention as a parent strain (AO-D-2 strain) for the duplicated translocation was finally obtained, wherein the 5' pyrG has been integrated into the B-locus of the $2^{nd}$ chromosome and the 3' pyrG has been integrated into the 166-locus of the $4^{th}$ chromosome.

Production of the Strains Having the Translocation of the Duplicated Region in its Chromosome Due to Ultraviolet Irradiation The strains having the translocation of the duplicated region in its chromosome due to ultraviolet irradiation were produced as follows.

Suspension containing about $2\times10^6/1000$ of conidium was applied on each of six malt plates, each of which was then placed in an open clean bench and irradiated by means of UV lamp for 0, 1, 2, 3, 4 and 5 minutes, respectively.

Figure 5:
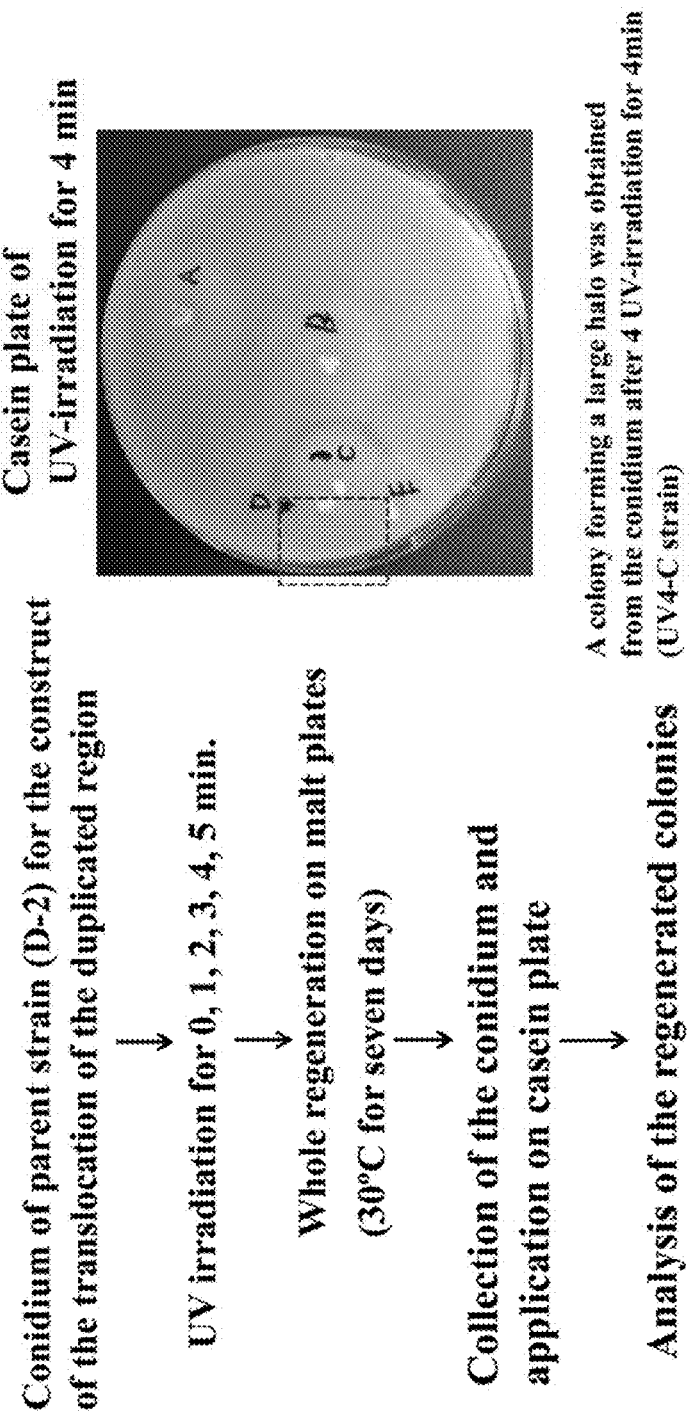
FIG. 5 shows the results of the production of the strains having the translocation of the duplicated region in its chromosome due to ultraviolet irradiation.

After the irradiation had been finished, the conidium was allowed to form on the whole part of the plate during the culture at 30° C. for a week. The Tween (0.01%) was then added to the thus formed conidium so that the condinium could be scratched by a spreader. The thus collected conidium was applied to casein plate at an amount of about $2\times10^6$/palte, cultured at 30° C. for about four weeks so as to check the growing condition of the conidium and halo. Since an uridine-auxotrophy strain could not grow on the casein plate, the growing strains were those such auxotrophy had been eliminated. The number of conidium (colonies) regenerated by the UV-irradiation was shown in FIG. 5. One colony was formed after UV-irradiation for 3 and 5 minutes, and five colonies were formed after UV-irradiation for 4 minutes. FIG. 5 also shows the casein plate applied with the conidium formed after the UV-irradiation for 4 minutes. One colony (UV4-C) showed the formation of a large halo out of the five colonies (UV4-A, UV4-B, UV4-C, UV4-D, and UV4-E).

Figure 6:
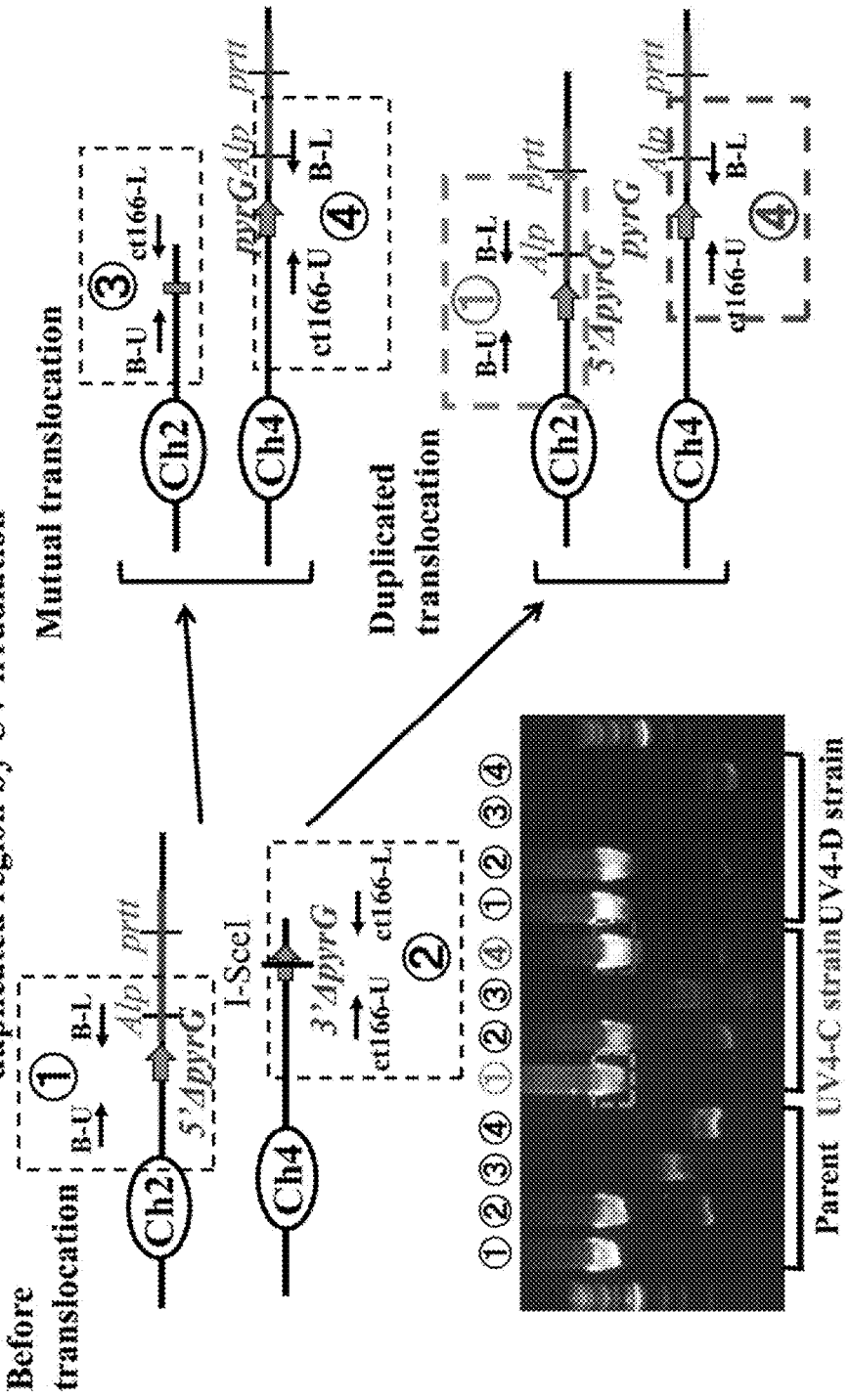
FIG. 6 shows the results of PCR showing acquisition of the strain having the translocation of the duplicated region in its chromosome due to ultraviolet irradiation.

Confirmation of the Translocation of the Duplicated Region in the Chromosome with PCR The resulting candidates were examined with PCR in order to confirm that the translocation of the duplicated region had been generated at a desired site. The sequences used for that were shown in Table 2. The presence of the duplicated translocation could be confirmed by the existence of an amplified product in PCR using the primers for both of the regions adjacent to the translocation region in each of the $2^{nd}$ and $4^{th}$ chromosome as shown in FIG. 6. Before the translocation, a band of about 5 kb would be amplified using the combination (1) of the primers B-U and B-L complementary to both sides of the 5' ΔpyrG in the $2^{nd}$ chromosome, and the combination (2) of the primers ct166-U and ct166-L complementary to both sides of the 3' ΔpyrG in the $4^{th}$ chromosome. After the mutual translocation (translocation only), the band would be amplified using the combination (3) of the primers B-U and ct166-L, and the combination (4) of the primers ct166-U and B-L. On the other hand, after the duplicated translocation, it was conceived that the band would be amplified by using the combination (1) of the primers B-U and B-L and the combination (4) of the primers ct166-U and B-L. The genomic DNA was prepared from the parent strain before the translocation and from the candidate strains, UV4-C and UV4-D, and was subjected to PCR. It was then confirmed that in the parent and UV4-D strains the amplification of the band was observed only when using the combinations (1) of the primers B-U and B-L of and (2) of the primers ct166-U and ct166-L, showing that the translocation did not occur. On the other hand, it was confirmed that in the UV4-C strain the amplification of the band was observed when using the combination (4) of the primers ct166-U and B-L in addition to the combination (1) of the primers B-U and B-L, suggesting that the duplicated translocation did occur in the target region (FIG. 6, the results of electrophoresis).

Confirmation of the Number of Copies with Real-Time PCR

Figure 7:
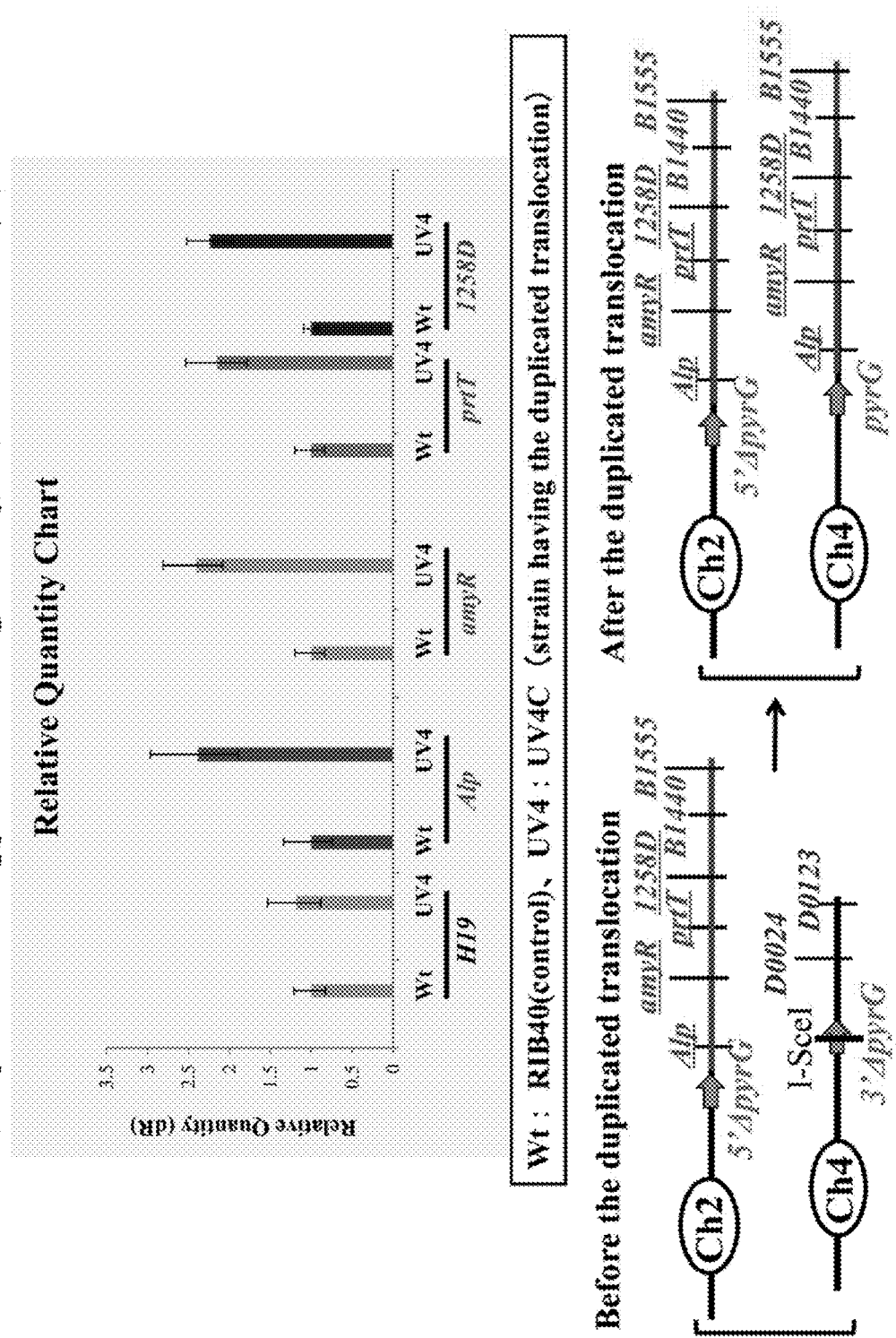
FIG. 7 shows the results of the analysis (1) of the numbers of copies of each gene by means of real time PCR in the strain having the translocation of the duplicated region in its chromosome due to ultraviolet irradiation.
Figure 8:
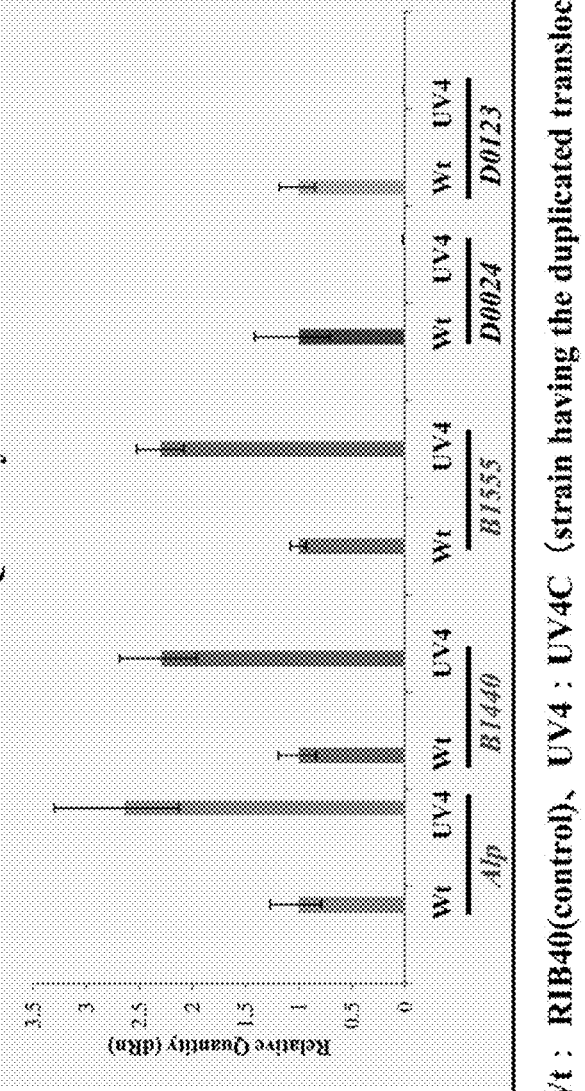
FIG. 8 shows the results of the analysis (2) of the numbers of copies of each gene by means of real time PCR in the strain having the translocation of the duplicated region in its chromosome due to ultraviolet irradiation.

The numbers of copies of each gene in the duplicated region of the $2^{nd}$ chromosomes were compared between the control strain (Wt: RIB40 strain) and the UV4-C strain having the translocation of the duplicated region by means of real-time PCR (quantitative PCR) with SYBR Green (FIGS. 7 and 8). The comparison was made by means of the relatively quantitative method using rad52 as a mormalizer, which was present in the other chromosome and its number of copy is one, with respect to B1036 (Alp) gene located at the end of the centromere side in the duplicated region, B1208 (amyR) gene located apart from the B1036 gene by 490 kb, B1212 (prtT) gene, B1258 (1258D) gene, B1440 gene, and B1555 gene located at the end of the telomere side in the duplicated region, and H19 gene in the $8^{th}$ chromosome that is located outside of the duplicated region as well as D0024 gene and D0123 gene located in the $4^{th}$ chromosome as the target for the translocation (FIG. 3). FIGS. 7 and 8 shows a relative value for the copy number in the control strain, Wt: RIB40 strain.

It was confirmed that while the value of about one was not changed for the copy number with respect to the H19 gene in the $8^{th}$ chromosome (outside of the duplicated region), the value was increased up to about 2 for the copy number with respect to the B1036 (Alp) gene, B1208 (amyR) gene, B1212 (prtT) gene, B1258 (1258D) gene in the UV4-C strain having the translocation of the duplicated region (FIG. 7).

It is also confirmed that while the value was increased up to about 2 for the copy number with respect to B1440 gene and B1555 gene that were located in the duplicated region, the value of almost zero were indicated for the copy number with respect to D0024 gene and D0123 gene located in the region between the 166 locus and the telomere in the $4^{th}$ chromosome as the target for the translocation (FIG. 8). These results demonstrated that the target region in the $2^{nd}$ chromosome was duplicated and translocated to the desired region in the $4^{th}$ chromosome.

Determination of Protease Activity and α-Amylase Activity in the Strain Having the translocation of the duplicated region Patent Literature 1 reported that a remarkable increase of the protease activity and amylase activity was observed in the strain having the duplication of genomic region corresponding to the region of A0090003001003~A0090003001259 genes in SC003 of the 2nd chromosome of *Aspergillus oryzae*. The above activities were therefore determined with respect to the strain having the translocation of the duplicated region in the 2nd chromosome in this Example.

Results of Determination of Protease Activity

Determination of a total protease activity was done using the enzyme extract obtained from the wheat-bran koji mold according to the method mentioned above so as to compare it between the control strain (Ct strain) and the strain having the translocation of the duplicated region. The results are shown in Table 3. The protease activity had been increased about 2.6 times higher in the UV4-C strain than in the control strain (Ct strain).

TABLE 3

| Protease Activity | |
|---|---|
| Strain | Relative Value |
| UV4-C | 2.6 |
| Ct | 1 |

Results of Determination of α-Amylase Activity

Determination of α-amylase activity was done using the same enzyme extract. The results are shown in Table 4. The α-amylase activity had been increased about 1.8 times higher in the UV4-C strain than in the control strain.

TABLE 4

| Amylase Activity | |
|---|---|
| Strain | Relative Value |
| UV4-C | 1.8 |
| Ct | 1 |

Accordingly, it was confirmed that the UV4-C strain the translocation of the duplicated region according to the present invention showed the significant increase in the protease and α-amylase activities in the wheat-bran culture, showing that a wide region in the $2^{nd}$ chromosome comprising the alkaline protease gene was duplicated in said strain.

The above results obtained with respect to the UV4-C strain in the PCR, real-time PCR (quantitative PCR) and the determination of the activities in the culture with the wheat-bran showed that the part comprising alp, amyR and prtT genes in the $2^{nd}$ chromosome (the 1,380 kb region comprising a part corresponding to the ORF regions of A0090003001035~A0090003001556 in SC003 region) was duplicated and translocated to the telomere side of the boundary region between A0090166000009~A0090166000010 (166 locus), increasing the number of copies of the above genes.

Example 2

Production of the Strains Having the Translocation of the Duplicated Region in its Chromosome Due to Site-Specific Cleavage The production of the transformant, preparation of the 5' ΔpyrG and 3' ΔpyrG, and construction of a vector for integrating 5' ΔpyrG unit into the B locus in the $2^{nd}$ chromosome were carried out in the same way as in Example 1.

Construction of a Vector for Integrating 3' ΔpyrG Unit into the 166 Locus in the 4th Chromosome Then, the vector for integrating 3' ΔpyrG unit into the 166 locus in the $4^{th}$ chromosome was constructed as follows.

A DNA fragment of 3 kb comprising a part adjacent to the B locus was obtained with PCR using the primers 166-U and 166-L and the genomic DNA of *Aspergillus oryzae* RIB40 strain as a template. The resulting fragment was purified and subjected to a cloning by means of TOPO-TA cloning kit (invitrogen). A DNA fragment of about 6 kb was then prepared by amplification using the primers 166-iU and 166-iL, and the resulting plasmid as a template. The 3' ΔpyrG unit comprising I-SceI cleavage site in its coding region was then amplified using the primers P-U and P-L to give a fragment of about 3 kb. These fragments were purified and treated by In-fusion cloning kit (Takara) to give a vector p166-d3pyrG-I.

Construction of a Parent Strain for the Duplicated Translocation

The resulting vectors were integrated into the B-locus and 166-locus of *Aspergillus oryzae*, respectively, to give a transformant for the duplicated translocation.

First, *Aspergillus oryzae* RP-1 strain (ΔpyrG) was transformed with a fragment obtained by the amplification of the vector pB-d5pyrG with the primers B-U and B-L. The transformants grown on the regeneration medium was screened with the primers B-OU and B-OL to obtain a strain comprising the vector integrated into the B-locus. Conidium was collected from the strain and applied on the CZ medium plate containing 5FOA. After culture for about one week at 30° C., DNA was extracted from a resistant strain having produced a lot of adhering conidium and subjected to PCR using the primers B-OU and B-OL to confirm the deficiency of the terminal part at the 5' end of pyrG so that the strain could not grow in the minimum medium. A strain having the 5' ΔpyrG integrated in the B-locus (AO-B-d5pyrG strain) was thus obtained.

Then, the resulting AO-B-d5pyrG strain was transformed with a fragment obtained by the amplification of the vector p166-d3pyrG with the primers 166-U and 166-L. The transformants regenerated on the minimum medium was screened with the primers 166-OU and 166-OL to obtain a strain comprising the vector integrated into the 166-locus. Conidium was collected from the strain and applied on the CZ medium plate containing 5FOA. After culture for about one week at 30° C., DNA was extracted from a resistant strain having produced a lot of adhering conidium and subjected to PCR using the primers 166-OU and 166-OL to confirm the deficiency of the terminal part at the 3' end of pyrG and the integration of the cleavage recognition site with I-SceI so that the strain could not grow in the minimum medium. Thus, a transformant according to the present invention as a parent strain (AO-BN43 strain) for the duplicated translocation was finally obtained, wherein the 5' ΔpyrG has been integrated in the B-locus of the $2^{nd}$ chromosome and the 3' ΔpyrG has been integrated in the 166-locus of the $4^{th}$ chromosome.

Production of the Strains Having the Translocation of the Duplicated Region in its Chromosome Due to the Site-Specific Cleavage The strains having the translocation of the duplicated region in its chromosome were produced by means of the site-specific cleavage as follows. Conidium of the parent strain was inoculated into Polypeptone dextrin (PD) liquid and cultured at 30° C. for 14 hours. The protoplast was prepared in the same way as in the transformation and subjected to the treatment with I-sect as described in the Experimental Methods. The protoplast was placed on the 1.2M sorbitol CZ medium plate and subjected to static culture at 30° C. for about a week to give a regenerated strain, BN1-1 strain. As the parent strain had uridine-auxotrophy, it could not grow as it was. On the other hand, it was expected that 3' ΔpyrG integrated in the $4^{th}$ chromosome that had been cleaved by I-SceI would be repaired and compensated with 5' ΔpyrG integrated in the $2^{nd}$ chromosome to give the whole ΔpyrG.

Confirmation of the Translocation of the Duplicated Region in the Chromosome with PCR The resulting candidates were examined with PCR in order to confirm that the translocation of the duplicated region had been generated at a desired site. The sequences used for that were shown in Table 2. The presence of the duplicated translocation could be confirmed by the existence of an amplified product in PCR using the primers for both of the regions adjacent to the translocation region in each of the $2^{nd}$ and $4^{th}$ chromosome as shown in FIG. 9. Before the translocation, a band of about 5 kb would be amplified using the combination (1) of the primers B-U and B-L complementary to both sides of the 5' ΔpyrG in the $2^{nd}$ chromosome, and the combination (2) of the primers ct166-U and ct166-L complementary to both sides of the 3' ΔpyrG in the $4^{th}$ chromosome. After the mutual translocation (translocation only), the band would be amplified using the combination (3) of the primers B-U and ct166-L, and the combination (4) of the primers ct166-U and B-L. On the other hand, after the duplicated translocation, it was conceived that the band would be amplified by using the combination (1) of the primers B-U and B-L and the combination (4) of the primers ct166-U and B-L. The genomic DNA was prepared from candidate strain, BN1-1 strain, and was subjected to PCR. It was then confirmed that the amplification of the band was observed only when using the combination (1) of the primers B-U and B-L of and the combination (4) of the primers ct166-U and B-L, but not when using the combination (2) of the primers ct166-U and ct166-L and the combination (3) of the primers B-U and ct166-L, suggesting that the duplicated translocation did occur in the target region (FIG. 9, the results of electrophoresis).

Confirmation of the Number of Copies with Real-Time PCR

The numbers of copies of each gene in the duplicated region of the $2^{nd}$ chromosomes were compared between the control strain (Wt: RIB40 strain) and the BN1-1 strain having the translocation of the duplicated region by means of real-time PCR (quantitative PCR) with SYBR Green (FIGS. 10 and 11). The comparison was made by means of the relatively quantitative method using rad52 as a normalizer, which was present in the other chromosome and its number of copy is one, with respect to B1036 (Alp) gene located at the end of the centromere side in the duplicated region, B1212 (prtT) gene, B1440 gene, and B1555 gene located at the end of the telomere side in the duplicated region, and D0024 gene and D0123 gene located in the $4^{th}$ chromosome as the target for the translocation (FIG. 3) as well as H19 gene in the $8^{th}$ chromosome that is located outside of the duplicated region. FIGS. 10 and 11 shows a relative value for the copy number in the control strain, Wt: RIB40 strain.

It was confirmed that the value was increased up to about 2 for the copy number with respect to the B1036 (Alp) gene, B1212 (prtT) gene, B1440 gene, and B1555 gene in the BN1-1 strain. On the other hand, D0024 gene and D0123 gene located in the $4^{th}$ chromosome as the target for the translocation were eliminated in the BN1-1 strain (FIGS. 10 and 11). The value of about one was not changed with respect to the H19 gene in the $8^{th}$ chromosome (outside of the duplicated region).

Results of Determination of Protease Activity

Determination of a total protease activity was done in the same way as in Example 1 so as to compare it between the control strain (Ct strain) and the strain having the translocation of the duplicated region. The results are shown in Table 5. The protease activity had been increased about 2.5 times higher in the BN1-1 strain than in the control strain (Ct strain).

TABLE 5

| Protease Activity | |
|---|---|
| Strain | Relative Value |
| BN1-1 | 2.5 |
| Ct | 1 |

Results of Determination of α-Amylase Activity

Determination of α-amylase activity was done using the same enzyme extract. The results are shown in Table 6. The α-amylase activity had been increased about 1.5 times higher in the BN1-1 strain than in the control strain.

TABLE 6

| Amylase Activity | |
|---|---|
| Strain | Relative Value |
| BN1-1 | 1.5 |
| Ct | 1 |

The above results obtained with respect to the BN1-1 strain in the PCR, real-time PCR (quantitative PCR) and the determination of the activities in the culture with the wheat-bran showed that the part comprising alp, amyR and prtT genes in the $2^{nd}$ chromosome (the 1,380 kb region comprising a part corresponding to the ORF regions of A0090003001035~A00900003001556 in SC003 region) was duplicated and translocated to the telomere side of the boundary region between A0090166000009~A0090166000010 (166 locus), increasing the number of copies of the above genes.

Accordingly, it has been confirmed that it is now possible to duplicate and translocate any large region in the chromosome of the fungus belonging to *Aspergillus* across a wide range according to the present invention.

INDUSTRIAL APPLICABILITY

The method according to the present method has now made it possible to identify a chromosomal region considered to be important from a practical point of view based on the information about the genome of a fungus strain to be bred, and to produce a strain having the duplication of said chromosomal region. Accordingly, it is expected that an efficient molecular breeding will be developed, so as to produce *Aspergillus* strains wherein a new useful trait, which was completely unknown in the art, has been increased.

What is claimed is:

1. A transformant of a fungus belonging to *Aspergillus*, comprising,
   a first transformation marker gene fragment with a 3' terminal deficiency integrated in a reverse direction into the 5' end of a target region capable of duplicated translocation wherein the target region is located in a long arm of a first chromosome, or said marker gene fragment is integrated in a forward direction into the 3' end of a target region capable of duplicated translocation wherein the target region is located in a short arm of the first chromosome; and
   a second transformation marker gene fragment, which is the same as the first transformation marker gene fragment, except that it has a 5' terminal deficiency, integrated in a reverse direction into the 5' end of a region to be replaced with one of said target regions wherein the region to be replaced is located in a long arm of a second chromosome, or said marker gene fragment is integrated in a forward direction into the 3' end of a region to be replaced with one of said target regions wherein the region to be replaced is located in a short arm of the second chromosome;
   wherein a homologous sequence region is present in common in a middle portion of a coding region of both of the transformation marker gene fragments.

2. The transformant according to claim 1, wherein the transformation marker gene fragments are selected from the group consisting of pyrG, sC and niaD.

3. The transformant according to claim 1, further comprising a restriction enzyme recognition site in at least one of the homologous sequence regions.

4. The transformant according to claim 3, wherein the restriction enzyme recognition site is recognized by a restriction enzyme selected from the group consisting of I-sceI, I-ceuI, Pl-pspI and Pl-sceI.

5. The transformant according to claim 3, wherein the restriction enzyme recognition site has been introduced by a homologous recombination.

6. The transformant according to claim 1, wherein the fungus belonging to *Aspergillus* is *Aspergillus sojae* or *Aspergillus oryzae*.

7. A method for the production of duplicated translocation of an optional region in the chromosome of a fungus belonging to *Aspergillus*, comprising:

(a) culturing the transformant of claim 1;

(b) obtaining a fungus strain from the cultured transformant wherein the target region capable of duplicated translocation has been duplicated and translocated by homologous recombination between two different chromosomes via a repairing mechanism after a doublestrand break in homologous sequence regions that are present in common in the middle portion of the coding region of each of the transformation marker gene fragments of the transformant integrated into the two different chromosomes; and (c) selecting the fungus strain wherein the target region has been duplicated by means of a trait based on an intact transformation marker gene.

8. The method according to claim 7, wherein the transformant is in a multinuclear state.

9. The method according to claim 7, wherein the homologous recombination between two different chromosomes is induced by ultraviolet irradiation of the transformant.

10. The method according to claim 7, wherein the homologous recombination is induced by culturing the transformant with a restriction enzyme.

11. A fungus belonging to *Aspergillus* having translocation of the duplicated region in its chromosome, which is obtained by the method according to claim 7.

12. The fungus according to claim 11, wherein the fungus belonging to *Aspergillus* is *Aspergillus sojae* or *Aspergillus oryzae*.

13. The fungus according to claim 11, wherein the translocation of the duplicated region is one thousand kb or more.

14. Soy sauce produced by fermentation with the fungus belonging to *Aspergillus* according to claim 12.

15. The transformant according to claim 1, wherein the middle portion is about 100 bp to about 2 kb in length.

* * * * *